United States Patent
Wu et al.

(10) Patent No.: US 10,881,704 B2
(45) Date of Patent: Jan. 5, 2021

(54) **USAGE OF SEMEN *ZIZIPHI SPINOSAE* OIL IN THE TREATMENT OF MEDICINAL INSOMNIA**

(71) Applicant: SHIJIAZHUANG YILING PHARMACEUTICAL CO., LTD., Hebei (CN)

(72) Inventors: Yiling Wu, Hebei (CN); Shaohua Zhao, Hebei (CN); Meng Wang, Hebei (CN)

(73) Assignee: SHIJIAZHUANG YILING PHARMACEUTICAL CO., LTD., Shijiazhuang (CN)

( * ) Notice: Subject to any disclaimer, the term of this patent is extended or adjusted under 35 U.S.C. 154(b) by 0 days.

(21) Appl. No.: 16/075,891

(22) PCT Filed: Sep. 9, 2016

(86) PCT No.: PCT/CN2016/098521
§ 371 (c)(1),
(2) Date: Aug. 6, 2018

(87) PCT Pub. No.: WO2018/045547
PCT Pub. Date: Mar. 15, 2018

(65) Prior Publication Data
US 2019/0201471 A1    Jul. 4, 2019

(51) Int. Cl.
| | | |
|---|---|---|
| *A61K 36/725* | (2006.01) | |
| *G01N 30/02* | (2006.01) | |
| *A61P 25/20* | (2006.01) | |
| *G01N 30/00* | (2006.01) | |
| *A61K 9/48* | (2006.01) | |
| *A61K 45/06* | (2006.01) | |

(52) U.S. Cl.
CPC .......... *A61K 36/725* (2013.01); *A61K 9/4825* (2013.01); *A61K 45/06* (2013.01); *A61P 25/20* (2018.01); *G01N 30/00* (2013.01); *G01N 30/02* (2013.01); *A61K 2236/31* (2013.01); *A61K 2236/50* (2013.01); *G01N 2030/025* (2013.01)

(58) Field of Classification Search
None
See application file for complete search history.

(56) References Cited

FOREIGN PATENT DOCUMENTS

| CN | 1491693 | 4/2004 |
|---|---|---|
| CN | 101229247 | 7/2008 |
| CN | 103039962 | 4/2013 |
| CN | 104886568 | 9/2015 |

OTHER PUBLICATIONS

Yu-Juan et al. (2003) J. Chromatographic Sci. vol. 41: 41-43 (Year: 2003).*
Gao et al. (2013) J. Agric. Food Chem. 61: 3351-3363. (Year: 2013).*
Jiang et al. (2007) Nat. Prod. Res. vol. 21, Issue 4: 310-320. (Year: 2007).*
Shergis et al. (2017) Phytomedicine 34: 38-43. (Year: 2017).*
Shi et al. (2016) Sleep Medicine Reviews 29: 108-118. (Year: 2016).*
Wang et al. (2011) J. Am. Oil Chem. Soc. 88: 467-472. (Year: 2011).*
Wu, et al., "Study on GC Specific Chromatograms of the Oil in Semen Ziziphi spinosae by Supercritical CO2 Extraction", Chin. Hosp. Pharm. J., Jan. 2007, vol. 27, No. 1.
Wuxi Light Industry College, "Degumming and Deacidification", Oil Extraction and Processing, Agriculture Press, Dec. 31, 1986, pp. 234-239.
International Search Report, International Application No. PCT/CN2016/098521, dated Jun. 2, 2017.
Written Opinion, International Application No. PCT/CN2016/098521 (no translation).

* cited by examiner

*Primary Examiner* — Russell G Fiebig
(74) *Attorney, Agent, or Firm* — Burns & Levinson LLP; Christopher R. Cowles

(57) ABSTRACT

The present invention involves the application of Semen Ziziphi Spinosae oil in the preparation of drugs for treating medicinal insomnia. Semen Ziziphi Spinosae oil has a therapeutic effect on insomnia caused by ephedrine, prednisone and other drugs, and Semen Ziziphi Spinosae oil that is prepared within the pressing temperature of 80 to 100° C. has the best efficacy for treating medicinal insomnia.

14 Claims, 17 Drawing Sheets

USAGE OF SEMEN *ZIZIPHI SPINOSAE* OIL IN THE TREATMENT OF MEDICINAL INSOMNIA

RELATED APPLICATIONS

This application is the U.S. national stage pursuant to 35 U.S.C. § 371, of international application Ser. No. PCT/CN2016/098521 filed Sep. 9, 2016, designating the U.S., and published in Chinese on Mar. 15, 2018 as publication WO 2018/045547 A1, entitled "Applications of Jujube Seed Oil in Treating Medicinal Insomnia". The entire contents of the aforementioned patent application are incorporated herein by this reference.

TECHNICAL FIELD

The present invention involves a new usage of Semen Ziziphi Spinosae oil in the treatment of medicinal insomnia, belonging to the healthcare field.

BACKGROUND OF THE INVENTION

Semen Ziziphi Spinosae is the dry, mature seed of *Ziziphus jujuba* Mill. var. *spinosa* (Bunge) Hu ex H. F. Chou, first documented in Shen Nong's Herbal Classic and listed at a top grade. It is sour in taste and neutral in nature, attributive to the liver, gallbladder and heart meridians. It can tranquilize the mind by nourishing the heart, arrest sweating and promote fluid production and nourishing the liver and therefore is mainly used for treating insomnia with deficient restlessness, palpitation and dreaminess, hyperhidrosis due to body deficiency, consumption of body fluid and thirst, etc. Stir-fried Semen Ziziphi Spinosae has a stronger mind tranquilizing effect. As expounded in the *A Supplement to the Materia Medica*, "for hypersomnia, raw Semen Ziziphi Spinosae should be used; for insomnia, stir-fried Semen Ziziphi Spinosae should be used". Modern research has shown that, both semen Ziziphi Spinosae and stir-fried Semen Ziziphi Spinosae have sedative, hypnotic, analgesic, anticonvulsant, hypothermic, antihypertensive effects in pharmacology.

Sleep disorders refer to abnormal quantity and quality of sleep, or some clinical symptoms such as reduced sleep or hypersomnia that occur during sleep, among which insomnia is most commonly seen. Insomnia is a common disease, in which internal injury caused by emotions and diet, or post-illness and old age, innate deficiency, fright due to deficiency of heart-energy and other etiological factors lead to the lack of preservation of heart spirit or disquieted heart spirit, and consequently result in frequent incapability of getting normal sleep. Insomnia is not a critical illness, but it prevents people from normal living, work, study and health and can exacerbate or induce diseases such as palpitation, chest obstruction, vertigo, headache and stroke. Patients with refractory insomnia suffer from pain on a long-term basis and even form dependence on hypnotics, while long-term use of hypnotics causes iatrogenic diseases.

There are many causes of insomnia and the effects of drugs, such as antiasthmatic agents, diuretics, antihypertensive agents, anticholinergic agents, sedatives, bacteria, glucocorticoids, analgesics and antiarrhythmic agents, cannot be neglected. If insomnia or exacerbation of insomnia occurs during medication, medicinal insomnia should be considered first.

Contents of the Invention

As a part of the present invention, the usage of Semen Ziziphi Spinosae oil in the treatment of medicinal insomnia is provided.

The said drugs that can cause insomnia include antiasthmatic agents, antihypertensive agents, anticholinergic agents, sedatives, glucocorticoids, analgesics, antitubercu-lotic agents, antiarrhythmic agents, etc. Preferably, the said drugs that can cause insomnia include aminophylline, ephedrine, methyldopa, clonidine, atropine, belladonna, chloropromazine, diazepam, prednisone, dexamethasone, prednisolone, morphine, dolantin, isoniazid, diisopyramide, procaine, etc.

The said Semen Ziziphi Spinosae oil is an oil component that is extracted from Semen Ziziphi Spinosae.

In some embodiments, the said Semen Ziziphi Spinosae oil can be prepared by the extraction method with organic solvent (e.g. petroleum ether), pressing method or super-critical fluid extraction method.

As a preferred embodiment, the said Semen Ziziphi Spinosae oil can be prepared by the following method: Take Semen Ziziphi Spinosae, press at 80-100° C. and get the Semen Ziziphi Spinosae oil.

Preferably, the said Semen Ziziphi Spinosae is stir-fried before pressing.

Preferably, the Semen Ziziphi Spinosae oil obtained by pressing is further given degumming, deacidification, washing, dewatering and decolorization treatments.

In some embodiments, the said "degumming" adopts the following method: Add saline water into the Semen Ziziphi Spinosae oil according to the oil/water/salt ratio of (40-6):(2-5):(0.2-0.5), and stir; preferably, the said oil/water/salt weight ratio is 50:4:0.4. Further preferably, the oil temperature in this process should not exceed 80° C.

In some embodiments, the said "deacidification" adopts the following method: Add alkaline water into the "degummed" Semen Ziziphi Spinosae oil according to the oil/water/alkali ratio of (40-60):(1-3):(0.1-0.3), stir, precipitate the mixture overnight, and separate the oil from the precipitate; preferably, the said oil/water/alkali weight ratio is 50:2:0.2. Further preferably, the oil temperature in this process should not exceed 75° C.

In some embodiments, the said "washing" adopts the following method: Add water into the "deacidificated" Semen Ziziphi Spinosae oil according to the oil/water ratio of (40-60):(4-6), stir, stand still, remove the precipitate, and get the oil. Preferably, the said oil/water weight ratio is 50:5. Further preferably, the oil temperature in this process should not exceed 80° C.

The research of this invention shows that, Semen Ziziphi Spinosae oil has a therapeutic effect on insomnia caused by ephedrine, prednisone and other drugs. And Semen Ziziphi Spinosae oil prepared within the pressing temperature of 80 to 100° C. has the best efficacy for treating medicinal insomnia.

As a part of this invention, a preparation method of Semen Ziziphi Spinosae oil is provided, which comprises: Take Semen Ziziphi Spinosae, press at 80-100° C. and get the Semen Ziziphi Spinosae oil.

Preferably, the said Semen Ziziphi Spinosae is stir-fried before pressing.

Preferably, the Semen Ziziphi Spinosae oil obtained by pressing is further given degumming, deacidification, washing, dewatering and decolorization treatments.

In some embodiments, the said "degumming" adopts the following method: Add saline water into the Semen Ziziphi Spinosae oil according to the oil/water/salt ratio of (40-6):(2-5):(0.2-0.5), and stir; preferably, the said oil/water/salt weight ratio is 50:4:0.4. Further preferably, the oil temperature in this process should not exceed 80° C.

In some embodiments, the said "deacidification" adopts the following method: Add alkaline water into the "degummed" Semen Ziziphi Spinosae oil according to the oil/water/alkali ratio of (40-60):(1-3):(0.1-0.3), stir, precipitate the mixture overnight, and separate the oil from the precipitate; preferably, the said oil/water/alkali weight ratio is 50:2:0.2. Further preferably, the oil temperature in this process should not exceed 75° C. The said "alkali" is sodium hydroxide or potassium hydroxide.

In some embodiments, the said "washing" adopts the following method: Add water into the "deacidificated" Semen Ziziphi Spinosae oil according to the oil/water ratio of (40-60):(4-6), stir, stand still, remove the precipitate, and get the oil. Preferably, the said oil/water weight ratio is 50:5. Further preferably, the oil temperature in this process should not exceed 80° C.

In some embodiments, the said Semen Ziziphi Spinosae oil can be prepared into clinically acceptable oral dosage forms including tablet, hard capsule, soft capsule, granule, oral solution, oral suspension, oral emulsion, mucilage, oral liquid, pill, powder, etc. by conventional preparation process and adding conventional excipients. Preferably, the said Semen Ziziphi Spinosae oil should be prepared into soft capsule.

The preparation method of the said Semen Ziziphi Spinosae oil soft capsule include the following steps:

Step 1, preparation of capsule shell: Weigh gelatin, glycerol and purified water according to the ratio of 1:0.4:1, heat the glycerol and purified water to 60-70° C., add gelatin, and stir 1.5 to 2.5 h and make the mixture into uniform gelatin solution;

Step 2, Preparation of capsule content: Take Semen Ziziphi Spinosae oil, stir well and pass it through a 100-mesh sieve;

Step 3, Pelleting: Make capsules by pressing, with the content of each capsule 0.5 g in weight;

Step 4, Shaping;

Step 5, Drying.

Wherein the ambient temperature and relative humidity for the said steps 2-4 are 18-26° C. and 45-65%, respectively;

The shaping time for the said step 4 is 1.5-2 h;

The drying temperature, relatively humidity and drying time for the said step 5 are 28-40° C., ≤30% and 18-20 h, respectively.

The said "stir-fried" in this invention means to fry Semen Ziziphi Spinosae until it is bloated with the color is slightly deeper by the "simple stir-frying method" stipulated in the *Chinese Pharmacopoeia* 2010.

In the present invention, the said "degumming" means to remove the peptizing impurities in the oil and the said peptizing impurities refer to the sol system formed by phospholipid, protein and carbonyl diglyceride in the oil with triglyceride. The said "deacidification" means to move the free fatty acids in the oil.

In the prevent invention, the said "conventional excipients" include: fillers, disintegrants, lubricants, suspending agents, binders, sweetening agents, corrigents, preservatives, matrices, etc. Fillers include: starch, pregelatinized starch, lactose, mannitol, chitin, microcrystalline cellulose, sucrose, etc.; disintegrants include: starch, pregelatinized starch, microcrystalline cellulose, polyvinylpyrrolidone cross-linked, low-substituted hydroxypropyl cellulose, croscarmellose sodium, etc.; lubricants: magnesium stearate, sodium dodecyl sulfate, talc powder, silicon dioxide, etc.; suspending agents include: polyvinylpyrrolidone, microcrystalline cellulose, sucrose, agar, hydroxypropyl methylcellulose, etc.; binders include: starch slurry, polyvinylpyrrolidone, hydroxypropyl methylcellulose, etc.

The present invention further provides a fingerprint detection method for the fatty acid components of Semen Ziziphi Spinosae oil, wherein the said detection method adopts the gas chromatography, with the chromatographic conditions: nitrogen as carrier gas, injector temperature: 250-300° C.; detector temperature: 250-300° C.; temperature programming: initial column temperature 100-180° C., held for 3-8 min, then slowly increased to 200-250° C. at the rate of 2-3° C./min and held for 3-8 min.

Preferably, wherein quartz capillary column is adopted, the splitting ratio is 30-50:1; and the $N_2$ flow rate is 0.5-1 mL/min.

Preferably, the said temperature programming is: initial column temperature 150° C., held for 5 min, then slowly increased to 230° C. at the rate of 2.5° C./min and held for 5 min.

Preferably, the said splitting ratio is 50:1; $N_2$ flow rate is 1 mL/min; injector temperature: 270° C.; detector temperature: 270° C.

Preferably, the preparation method of the investigational product is: Take Semen Ziziphi Spinosae oil, abstract it by adding alkaline methanol solution, then extract the abstracted solution by adding organic solvent, take the organic solvent layer, dilute it and get the test solution.

SPECIFIC EMBODIMENTS

Figure 1:
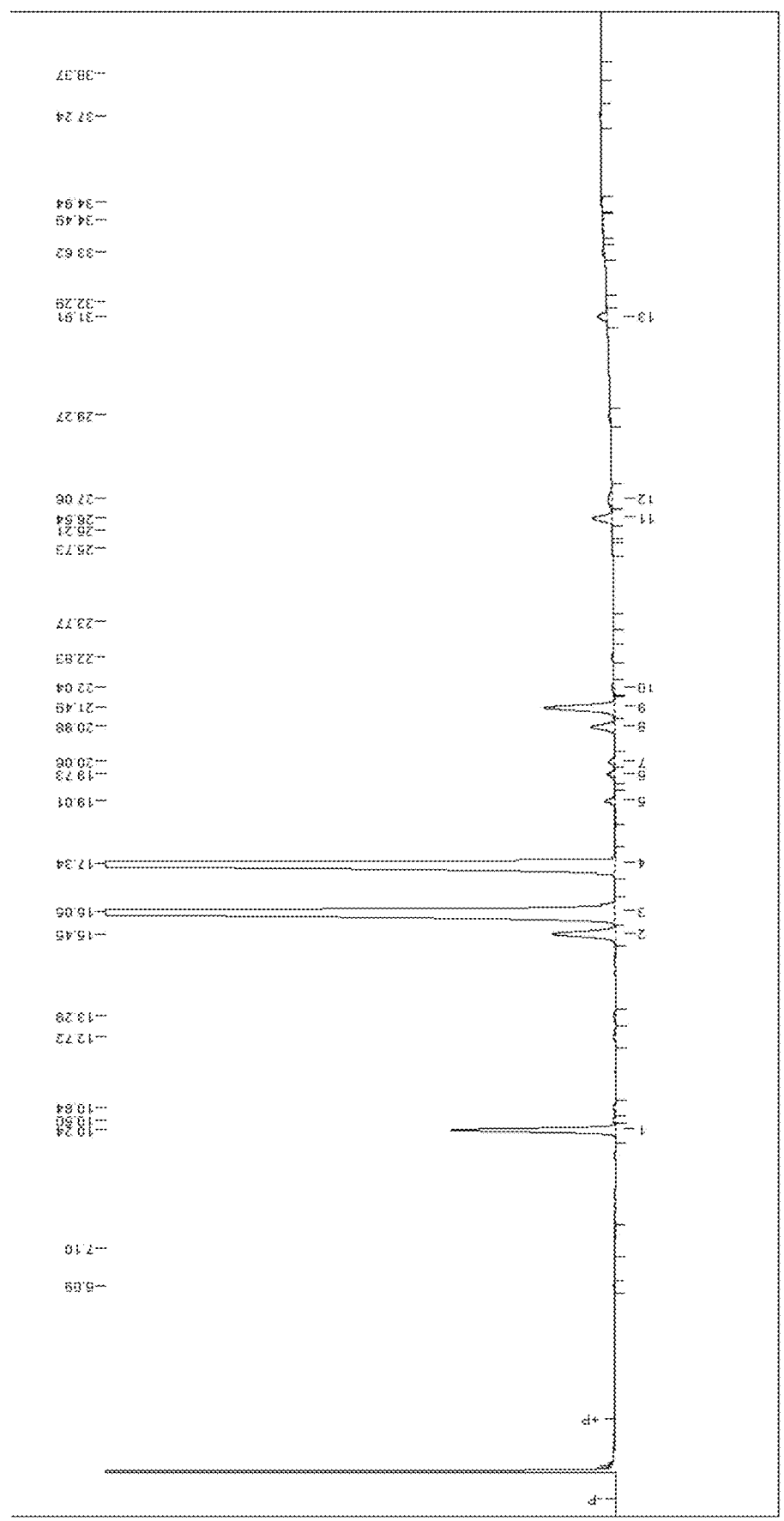
FIG. 1 Chromatogram of Semen Ziziphi Spinosae Oil Sample 1

Embodiment 1 Therapeutic Effect of Semen Ziziphi Spinosae Oil on Medicinal Insomnia 1. Experimental Animal Kunming mice, male, 18-22 g in weight;

2. Investigational Drugs:

Investigational drug 1: Semen Ziziphi Spinosae oil prepared according to Embodiment 2

Investigational drug 2: The preparation method is basically the same as that of Embodiment 2, except the pressing temperature is 50-60° C.

Drugs that caused insomnia: ephedrine, prednisone

3. Test Method:

60 mice were taken and placed into the laboratory for one week for acclimatization. Then they were randomly divided into 6 groups and dosed according to the drug and dosage in the table.

TABLE 1

Effects of Semen Ziziphi Spinosae Oil on the Length of Sleep of Mice with Medicinal Insomnia

| Group | Mice/n | Drug | Dosage |
|---|---|---|---|
| Blank group | 10 | — | — |
| Ephedrine group | 10 | Ephedrine | 4 mg/kg |
| Prednisone group | 10 | Prednisone | 1 mg/kg |
| Experiment 1 group | 10 | Ephedrine + Investigational drug 1 | Ephedrine: 4 mg/kg Investigational drug1: 167 mg/kg |
| Experiment 2 group | 10 | Ephedrine + Investigational drug 2 | Ephedrine: 4 mg/kg Investigational drug2: 167 mg/kg |
| Experiment 3 group | 10 | Prednisone + Investigational drug 1 | Prednisone: 1 mg/kg Investigational drug 1: 167 mg/kg |
| Experiment 4 group | 10 | Prednisone + Investigational drug 2 | Prednisone: 1 mg/kg Investigational drug 2: 167 mg/kg |

The investigational drug and insomnia-induced drugs were proportionally prepared into soybean oil solutions as investigational products, which were administered with via intragastric gavage with the intragastric volume calculated by 0.1 mL per 10 g body weight. The blank group was directly given soybean oil via intragastric gavage once daily, for consecutive 7 days. Mice were fasted at 8 h prior to the last dosing and given sodium pentobarbital (50 mg/kg) via intraperitoneal injection at 30 min after dosing, at the indoor temperature of 20° C. and the humidity of 40%. Measurements were made by using the righting reflex tester, the absence of righting reflex over 1 min was deemed as falling asleep, and the absence time and recovery time of righting reflex were observed and recorded. The duration from the absence of righting reflex to its recovery was the length of sleep.

4. Experimental Results
See Table 2 for the results:

TABLE 2

Effects of Semen Ziziphi Spinosae Oil on the Length of Sleep of Sodium Pentobarbital-induced Mice

| Group | Mice/n | Drug and Dosage | Length of Sleep (min) |
|---|---|---|---|
| Blank group | 10 | — | 95.3 ± 38.5 |
| Ephedrine group | 10 | Ephedrine: 4 mg/kg | 60.8 ± 25.3* |
| Prednisone group | 10 | Prednisone: 1 mg/kg | 68.4 ± 27.1* |
| Experiment 1 group | 10 | Ephedrine: 4 mg/kg Investigational drug1: 167 mg/kg | 125.7 ± 48.7# |
| Experiment 2 group | 10 | Ephedrine: 4 mg/kg Investigational drug2: 167 mg/kg | 100.3 ± 37.6#& |
| Experiment 3 group | 10 | Prednisone: 1 mg/kg Investigational drug 1: 167 mg/kg | 145.7 ± 51.8Δ |
| Experiment 4 group | 10 | Prednisone: 1 mg/kg Investigational drug 2: 167 mg/kg | 137.5 ± 49.5Δ$ |

Note:
*Compared to the blank group, P < 0.01;
compared to the ephedrine group, P < 0.01;
&compared to ephedrine + investigational drug 1 group, P < 0.01;
Δcompared to the prednisone group, P < 0.01;
$compared to the prednisone + investigational drug 1 group, P < 0.01.

It can be seen from Table 2 that, ephedrine and prednisone can significantly reduce the length of sodium pentobarbital-induced sleep in mice, while Semen Ziziphi Spinosae oil can significantly resist such reduced length of sleep caused by ephedrine and prednisone.

In addition, the above study results showed that, Semen Ziziphi Spinosae oil obtained by pressing at 80-100° C. has a therapeutic effect on medicinal insomnia significantly superior to that of Semen Ziziphi Spinosae oil obtained by pressing at 50-60° C.

Embodiment 2 Preparation of Semen Ziziphi Spinosae Oil

Take Semen Ziziphi Spinosae decoction pieces and feed them into the oil press machine via the injector, press them at a uniform speed (spindle speed 30-42 rpm) and a temperature of 80-100° C., filtrate the pressed Semen Ziziphi Spinosae crude oil under pressure via a 200-mesh filter cloth, and get the Semen Ziziphi Spinosae oil.

Embodiment 3 Preparation of Semen Ziziphi Spinosae Oil

The preparation method is basically the same as that of Embodiment 2, except the pressing temperature is 60-70° C.

Embodiment 4 Preparation of Semen Ziziphi Spinosae Oil

The preparation method is basically the same as that of Embodiment 2, except the pressing temperature is 130150° C.

Embodiments 2-4 Effects of Different Pressing Temperatures on the Oil Product State and Components of Semen Ziziphi Spinosae Oil

| Pressing Temperature | Oil Cake State | Oil Product State | Oil Yield | Oil Cake Residual Oil Rate | Total Oleic-linoleic Acid Amount |
|---|---|---|---|---|---|
| 60~70° C. | Loose | Light color | 8.22% | 14.08% | 83.7% |
| 80~100° C. | Shaped well | Light color | 14.23% | 8.80% | 92.5% |
| 130~150° C. | Fragile, with a burned odor | Deep color | 14.01% | 8.57% | 90.7% |

It can be seen from the above table that, when the pressuring temperature was excessively low (<70° C.), the oil cake was loose and the oil yield was significantly lower, causing waste of raw material. When the temperature was excessively high (130-150° C.), the resulting oil cake was fragile and burnt, and the oil product was relatively deep in color. However, when the pressing temperature was 100° C., the resulting oil cake was shaped well, the oil product was relatively light in color, the oil yield was relatively high and the oil cake residual oil rate was low, therefore, the pressing temperature should be controlled below 100° C., but not lower than 80° C. In addition, the total amount of oleic-linoleic acid was highest at the pressing temperature of 80-100° C.

Embodiment 5 Refinement of Semen Ziziphi Spinosae Oil a) Hydrated Degumming:
Hydrated degumming was carried out in the hydration tank: Transfer the Semen Ziziphi Spinosae oil crude product prepared by any one of Embodiments 2-4 into the hydration tank, heat and stir simultaneously, rise the oil temperature to about 60° C., stir the oil and add boiled saline water at the same time (oil/water/salt ratio=50 kg:4 kg:04. Kg), and stir 30 min after the saline water is added up, with the oil temperature not more than 80° C.

b) Deacidification by Alkali Refining:

Deacidification by alkali refining was carried out in the hydration tank: Stir degummed oil while adding boiled alkaline water (oil/water/sodium hydroxide ratio=50 kg:2 kg:0.25 kg), after which the oil temperature should not exceed 75° C., stir for another 1 h, drain the oil and let it precipitate overnight. Separate the oil from the precipitate the next day.

c) Washing:

Washing dealkalization was carried out in the hydration tank: Heat the deacidificated oil while stirring, and when the oil temperature is risen to 65-70° C., keep stirring and adding boiled water (oil/water ratio=50 kg:5 kg), after which the oil temperature should not exceed 80° C., stir for another 30 min, let the oil stand still and precipitate for 1 h, and discharge the impurities. Wash the oil twice for subsequent use.

d) Dewatering:

High-temperature dewatering was carried out in the water knock-out: Transfer the oil into a water knock-out, heat it to 120° C., and dewater by stirring for 1.5-2 h. When the oil is under a clear state after being cooled from 120° C. to room temperature, the dewatering is complete.

e) Decolorization:

Decolorization was done in the bleaching tank: Prepare the filter layer, pre-heat dewatered oil (100° C.) for 30 min, let the oil cool down to 60-70° C., and decolorize slowly.

Embodiment 6 Preparation of Semen Ziziphi Spinosae Oil Soft Capsules (1) Preparation of Capsule Shell Weight gelatin, glycerol and water according to the ratio of 1:0.4:1, feed the glycerol and purified water into the vacuum gelatin-melting tank, initiate the stirring arm, heat to 60-70° C., feed gelatin, stir 1.5-2.5 h and make the mixture into a uniform gelatin solution, stop stirring, expel bubbles at the vacuum degree of 0.05 to 0.08 MPa, discharge the gelatin solution, pass it through a 100-mesh sieve, inject it into an insulation barrel and keep the temperature at 60° C., let the solution stand still and defoam for 0.5-1.0 h, and put aside for subsequent use.

(2) Preparation of Capsule Content

Take the Semen Ziziphi Spinosae oil prepared in Embodiment, stir it well in the mixing tank, expel bubbles at the temperature <50° C. and the vacuum degree of 0.05-0.09 MPa, pass the oil through a 100-mesh sieve and put aside for subsequent use. Environmental requirements: 18-26° C., RH (relative humidity) 45-65%.

(3) Pelleting

Transfer the prepared content into the storage hopper of the pelleting press, deliver the prepared capsule shell gelatin solution into the gelatin solution box of the pelleting press, startup the pelleting machine, make gelatin capsules by pressing, with the thickness of capsule shell controlled and the content of each gelatin capsule 0.5 g in weight. The parameters of pelleting process are as follows: injector temperature: 35-45° C.; gelatin solution box temperature: 40-60° C.; engine speed: 0-4 r/min; capsule shell thickness: 0.7-0.9 mm; environmental requirements: 18-24° C., RH 45-65%.

(4) Shaping

After pelleting, let the soft capsules shape 1.5-2 h; the shaping conditions are 18-24° C. and RH 45-65%.

(5) Drying

Carry out dynamic drying on the shaped soft capsules under the conditions of 28-40° C. and RH≤30%, for 18-20 h.

Embodiment 7 Capsule Shell Ratio Screening

Capsules shells were prepared according to the gelatin/glycerol/water ratios of 1:0.3:1, 1:0.35:1, 1:0.4:1 and 1:0.5:1 respectively (the preparation method was the same as Embodiment 6) to investigate the fluidity of gelatin solution in the gelatin-melting process and the hardness and elasticity of resulting capsule shells, and the results showed that, when the gelatin/glycerol/water ratio was 1:0.3:1, the gelatin solution had a poor fluidity and was not easy to shape; when the ratio was 1:0.35:1, the gelatin solution had an ordinary fluidity and was capable of shaping, but the capsule shell formed was relatively hard; when the ratio was 1:0.4:1, the gelatin solution had a good fluidity, and the capsule shell formed was suitable and flexible; when the ratio was 1:0.5:1, the gelatin solution had a good fluidity and was capable of shaping, but the capsule shell formed was soft and fragile. Therefore, the gelatin/glycerol/purified water ratio was determined as 1:0.4:1.

According to the results of preliminary investigation, capsules shells were prepared according to the gelatin/glycerol/water ratio of 1:0.4:1 and prepared into soft capsules, and then the resulting soft capsule samples were given a 6-month ordinary-temperature investigation with the appearance and disintegration time of capsules as the outcome measures. The results are as follows:

| Investigated Months | Capsule Appearance | Disintegration Time (≤60 min) |
| --- | --- | --- |
| 0 | Bright color, suitable hardness | Qualified |
| 1 | Bright color, suitable hardness | Qualified |
| 2 | Bright color, suitable hardness | Qualified |
| 3 | Bright color, suitable hardness | Qualified |
| 6 | Bright color, suitable hardness | Qualified |

Judged according to the results of the 6-month ordinary-temperature observation above, capsule shells prepared at the gelatin/glycerol/water ratio of 1:0.4:1 had good characters and qualified disintegration, and the resulting capsules had a suitable hardness.

All the investigational drugs used in the Embodiments 8-10 below were Semen Ziziphi Spinosae oil that was refined by using Semen Ziziphi Spinosae crude oil prepared in Embodiment 2 according to the method specified in Embodiment 5 and was prepared into soft capsules according to the method in Embodiment 6.

Embodiment 8 Test of Semen Ziziphi Spinosae Oil in the Improvement of Sleep Function 1. Investigational Drug Take the content of Semen Ziziphi Spinosae oil, use edible soybean oil as the solvent when performing the experiment, and prepare the samples into different doses.

2. Experimental Animal

Experimental ICR mice were provided by Shanghai Slac Laboratory Animal Co., Ltd. with the Laboratory Animal Production License No. SOCK(HU)2012-0002, at the SPF grade, male, 20±2 g in weight. The feed was provided by Zhejiang Laboratory Animal Center with the Laboratory Animal Usage License No. SYXK(ZHE)2013-0190.

Testing environment conditions: Barrier environment, temperature 20-24° C., RH 40-70%. Before the test, the animals were acclimatized in the animal room environment for 4 days.

3. Dosage Design

The experiment set 3 dose groups and one solvent control group (soybean oil). The doses of the low-dose, medium-dose and high-dose groups were 83.3, 166.7 and 500.0 mg/kg body weight, respectively, equivalent to 5, 10 and 30 times the recommended human dose (1.0 g/60 kg body weight each day), respectively. 0.5, 1.0 and 3.0 g samples were weighed separately, added with soybean to 60 mL and prepared into 8.3, 16.7 and 50.0 mg/mL solutions as investigational products. The investigational products were administered via intragastric gavage at the volume of 0.1 mL/10 g body weight.

4. Experimental methods 4.1 Direct sleep experiment

40 ICR mice were taken, randomly divided into four groups (10 in each) and given intragastric gavage of investigational products once daily, for consecutive 30 days. The control group was given soybean oil by the same administration method as the investigational product groups. At the end of the experiment, direct sleep phenomenon in each group was observed by using back lying of mice for 1 min without righting, i.e. absence of righting reflex as the judging criterion of falling asleep and the duration from the absence of righting reflex to its recovery as the length of sleep to observe the number of animals falling asleep and their length of sleep after intragastric gavage.

4.2 Sodium Pentobarbital Sleep Time Prolongation Test:

40 ICR mice were taken, randomly divided into four groups (10 in each) and given intragastric of investigational products once daily, for consecutive 30 days. The control group was given soybean oil by the same administration method as the investigational product groups. At 20 min after the last intragastric gavage, animals in each group were given intraperitoneal injection of sodium pentobarbital (50 mg/kg body weight) at the injection volume of 0.1 mL/10 g body weight, and the absence of righting reflex was used as the judging criterion of falling asleep and the duration from the absence of righting reflex to its recovery as the length of sleep to observe the length of sleep of animals in each group.

4.3 Sodium Pentobarbital Subthreshold Dosage Hypnosis Test

40 ICR mice were taken, randomly divided into four groups (10 in each) and given intragastric of investigational products once daily, for consecutive 30 days. At 20 min after the last intragastric gavage, animals in each group was given intraperitoneal injection of sodium pentobarbital (35 mg/kg body weight) at the injection volume of 0.1 mL/10 g body weight, and the absence of righting reflex over 1 min was used as the judging criterion of falling asleep to observe the number of animals falling asleep within 30 min after administration of sodium pentobarbital in each group.

4.4 Sodium Pentobarbital Sleep Latency Test

40 ICR mice were taken, randomly divided into four groups (10 in each) and given intragastric of investigational products once daily, for consecutive 30 days. At 20 min after the last intragastric gavage, animals in each group was given intraperitoneal injection of uranium barbital (280 mg/kg body weight) at the injection volume of 0.1 mL/10 g body weight, and the absence of righting reflex was used as the judging criterion of falling asleep to observe the sleep latency profile of animals in each group.

4.5 The SPSS11.5 software package was adopted for data processing and statistics.

5 Experimental Results 5.1 Effects of Semen Ziziphi Spinosae Soft Capsules on the Direct Sleep of Mice See Table 3 for the results. The length of sleep and number of falling-asleep animals were 0 in the solvent group (soybean oil) and the three dose groups.

TABLE 3

Effects of investigational products on the Direct Sleep of Mice

| Group | Number of Animals (n) | Length of Sleep (sec) | Number of Falling-asleep Animals (n) |
|---|---|---|---|
| Solvent control group | 10 | 0 ± 0 | 0 |
| Low-dose group | 10 | 0 ± 0 | 0 |
| Medium-dose group | 10 | 0 ± 0 | 0 |
| High-dose group | 10 | 0 ± 0 | 0 |

5.2 Effects of Semen Ziziphi Spinosae Oil on Prolonging the Length of Sodium Pentobarbital Sleep in Mice See Table 4 for results. The original data met the requirement for homogeneity of variance (P>0.05) and compared to the solvent control group (soybean oil), the length of sodium pentobarbital sleep of mice in the high-dose group was prolonged and the difference was significant (q test, P<0.05).

TABLE 4

Effects of investigational products on the Prolongation of Length of Sodium Pentobarbital Sleep in Mice (X ± s)

| Group | Number of Animals (n) | Length of Sleep (sec) |
|---|---|---|
| Solvent control group | 10 | 1044 ± 568 |
| Low-dose group | 10 | 1710 ± 774 |
| Medium-dose group | 10 | 1618 ± 691 |
| High-dose group | 10 | 2029 ± 745# | q test: Compared to the solvent control group, #P<0.05

5.3 Effects of Semen Ziziphi Spinosae Soft Capsules on the Hypnotic Action of Sodium Pentobarbital Subthreshold Dose in Mice See Table 5 for the results. The original data met the requirements of $X^2$ test and comparing the number of animals falling asleep under the hypnotic action of sodium pentobarbital subthreshold dose between the three dose groups and the solvent control group (soybean oil), the differences were not significant ($X^2$ test, P>0.05).

TABLE 5

Effects of investigational products on the Hypnotic Action of Sodium Pentobarbital Subthreshold Dose in Mice

| Group | Number of Animals (n) | Number of Falling-asleep Animals (n) |
|---|---|---|
| Solvent control group | 10 | 2 |
| Low-dose group | 10 | 2 |
| Medium-dose group | 10 | 4 |
| High-dose group | 10 | 4 |
| F | | 1.905 |
| P | | 0.592 |

5.4 Effects of Semen Ziziphi Spinosae Soft Capsules on the Sodium Pentobarbital Sleep Latency of Mice See Table 6 for the results. All the original data met the requirement for homogeneity of variance (P>0.01) and compared to the solvent control group (soybean oil), the uranium barbital sleep latency of mice in the high-dose group was shortened and the difference was significant (q test, P<0.05).

TABLE 6

Effects of investigational products on Uranium Barbital Sleep Latency of Mice (X ± s)

| Group | Number of Animals (n) | Sleep Latency (sec) |
|---|---|---|
| Solvent control group | 10 | 2816 ± 722 |
| Low-dose group | 10 | 1919 ± 767 |
| Medium-dose group | 10 | 2153 ± 802 |
| High-dose group | 10 | 1656 ± 350* |
| F | | 5.261 |
| P | | 0.004 | q test: Compared to the solvent control group, #P<0.05

5.5 Effects of Semen Ziziphi Spinosae Soft Capsules on the Body Weight of Mice

See Tables 7-9 for the results. Tables 7, 8 and 9 show the body weights of mice in the sodium pentobarbital sleep time prolongation test, in the direct sleep test and sodium pentobarbital subthreshold hypnosis test, and in the barbital uranium barbital sleep latency test, respectively. All the original data met the requirement for homogeneity of variance (P>0.05) and compared to the solvent control group (soybean oil), the body weights of mice in each dose group at the early stage, mid-term and end stage of the test were not significantly different (analysis of variance, P>0.05).

TABLE 7

Body Weights of Mice in the Sodium Pentobarbital Sleep Time Prolongation Test

| Group | Number of Animals (n) | Early Weight (g) | Mid-term Weight (g) | End Weight (g) |
|---|---|---|---|---|
| Solvent control group | 10 | 20.6 ± 0.9 | 27.4 ± 2.0 | 30.6 ± 3.0 |
| Low-dose group | 10 | 20.8 ± 1.1 | 28.5 ± 2.5 | 30.9 ± 2.7 |
| Medium-dose group | 10 | 20.5 ± 1.0 | 27.6 ± 1.8 | 30.3 ± 1.8 |
| High-dose group | 10 | 20.7 ± 0.8 | 27.5 ± 1.6 | 30.6 ± 2.4 |
| F value | | 0.152 | 0.638 | 0.107 |
| P value | | 0.928 | 0.596 | 0.956 |

TABLE 8

Body Weights of Mice in the Direct Sleep Test and the Sodium Pentobarbital Subthreshold Dose Hypnosis Test

| Group | Number of Animals (n) | Early Weight (g) | Mid-term Weight (g) | End Weight (g) |
|---|---|---|---|---|
| Solvent control group | 10 | 20.9 ± 0.9 | 27.6 ± 2.0 | 30.7 ± 1.9 |
| Low-dose group | 10 | 20.4 ± 1.0 | 28.5 ± 2.1 | 31.4 ± 2.5 |
| Medium-dose group | 10 | 20.5 ± 1.2 | 27.0 ± 1.7 | 29.6 ± 2.4 |
| High-dose group | 10 | 20.6 ± 0.9 | 29.2 ± 1.3 | 32.2 ± 2.0 |
| F value | | 0.498 | 2.769 | 2.349 |
| P value | | 0.686 | 0.056 | 0.089 |

TABLE 9

Body Weights of Mice in the Uranium Barbital Sleep Latency Test

| Group | Number of Animals (n) | Early Weight (g) | Mid-term Weight (g) | End Weight (g) |
|---|---|---|---|---|
| Solvent control group | 10 | 20.5 ± 1.0 | 28.7 ± 1.5 | 31.6 ± 2.2 |
| Low-dose group | 10 | 20.5 ± 0.7 | 28.5 ± 1.8 | 30.6 ± 2.4 |
| Medium-dose group | 10 | 20.9 ± 0.9 | 27.7 ± 1.3 | 30.4 ± 2.0 |
| High-dose group | 10 | 20.6 ± 0.8 | 28.3 ± 1.8 | 30.7 ± 3.3 |
| F value | | 0.390 | 0.779 | 0.416 |
| P value | | 0.761 | 0.513 | 0.743 |

Embodiment 9 30-Day Semen Ziziphi Spinosae Oil Feeding Test

1 Materials and Methods 1.1 Sample and treatment: Take the content of Semen Ziziphi Spinosae oil, use edible soybean oil as the solvent and prepare the sample into different doses.

1.2 Experimental animal and testing conditions: The experimental SD rats were provided by Shanghai Slac Laboratory Animal Co., Ltd. with the Production License No. SCXK(HU)2012-0002, at the SPF grade, 50-70 g in weight. The feed for the experimental animals was provided by Zhejiang Laboratory Animal Center which follows the standard GB14924.1-2001. Testing environment conditions: Barrier environment, Laboratory Animal Room Usage License No. SYXK(ZHE)2013-0190, range of temperature 22-25° C., and range of relative humidity 50-70%. Before the test, the animals were acclimatized in the animal room environment for 4 days.

1.3 Methods 1.3.1 Dosage design: The recommended human dose of this product is 1.0 g/60 kg/day. The experiment set three dose groups and one solvent control group (edible soybean oil), among which the low, medium and high doses were 0.42, 0.83 and 1.67 g/kg body weight, respectively, equivalent to 25 times, 50 times and 100 times the recommended human dose. 21.0, 41.5 and 83.5 g of samples were taken separately, prepared into 0.084, 0.166 and 0.334 g/mL by adding edible soybean oil to 250 ml and administered orally via intragastric gavage each day according to 5 mL/kg body weight for consecutive 30 days.

1.3.2 Experimental method: 80 SD rats were taken and randomly divided into 4 groups (20 in each, 10 males and 10 females). Each rat was caged alone and ate and drank freely. They were observed for consecutive 30 days. Each week their body weight was recorded twice and feed intake was measured twice to calculate the food utilization rate. At the end of the experiment, the animals' last body weight (week 4 body weight) was measured and then they were fasted overnight. Fasting body weight was measured the next day and then blood was collected from their jugular vein. Hematological indexes were measured by Sysmex 1800i Automated Hematology Analyzer and blood biochemistry indexes were measured by TBA-40FR Automated Biochemical Analyzer. All the animals were given gross anatomy. Liver, kidneys, spleen and testes (ovaries) were taken and weighed to calculate the organ/body weight ratios. Liver, kidneys, spleen, stomach, intestine and testes (ovaries) were given histopathological examination (paraffin section, H-E staining, light microscopy).

1.3.3 Analysis of results: statistical analysis by SPSS11.5. The data was given homogeneity of variance test first. If the variance was homogeneity, one-way analysis of variance was adopted for comparison. If the original data did not meet the requirement for homogeneity of variance, rank sum test was adopted instead.

2 Results 2.1 In the general observation experiment, none of the rats in each group showed any abnormal symptom or sign, or died.

2.2 Effects on the Body Weight of Rats

See Table 10 for the results. The original data met the requirement for homogeneity of variance (P>0.05) and compared to the solvent control group, the body weights of rats in the three dose groups at different time points of the experiment were not significantly different (analysis of variance, P>0.05).

TABLE 10

Effects of Semen *Ziziphi Spinosae* Soft Capsules on the Body Weight of Rats (X ± s)

| Gender | Dosage | Number of Rats (n) | Early Weight (g) | Week 1 (g) | Week 2 (g) | Week 3 (g) | Week 4 (g) |
|---|---|---|---|---|---|---|---|
| Female | Solvent control group | 10 | 73.2 ± 4.9 | 113.5 ± 9.7 | 157.8 ± 11.2 | 195.3 ± 10.0 | 216.4 ± 11.7 |
| | Low-dose group | 10 | 73.1 ± 6.7 | 114.7 ± 11.0 | 157.1 ± 9.8 | 188.6 ± 11.3 | 209.3 ± 10.3 |
| | Medium-dose group | 10 | 70.9 ± 6.0 | 115.1 ± 7.9 | 159.0 ± 11.6 | 192.2 ± 11.1 | 210.1 ± 14.9 |
| | High-dose group | 10 | 71.9 ± 5.7 | 116.0 ± 8.7 | 163.2 ± 11.5 | 194.6 ± 13.2 | 216.9 ± 12.2 |
| | F | | 0.349 | 0.12 | 0.611 | 0.698 | 1.066 |
| | P | | 0.79 | 0.948 | 0.612 | 0.559 | 0.376 |
| Male | Solvent control group | 10 | 75.9 ± 6.1 | 124.6 ± 10.0 | 188.2 ± 11.0 | 254.4 ± 10.2 | 311.6 ± 13.7 |
| | Low-dose group | 10 | 76.7 ± 6.1 | 129.5 ± 9.2 | 190.1 ± 11.9 | 256.8 ± 16.6 | 318.2 ± 22.1 |
| | Medium-dose group | 10 | 75.8 ± 5.8 | 127.0 ± 13.9 | 192.4 ± 18.9 | 261.0 ± 19.9 | 321.1 ± 27.9 |
| | High-dose group | 10 | 75.4 ± 5.8 | 125.9 ± 10.4 | 185.1 ± 16.4 | 250.2 ± 20.9 | 310.3 ± 23.8 |
| | F | | 0.083 | 0.355 | 0.429 | 0.671 | 0.537 |
| | P | | 0.969 | 0.786 | 0.734 | 0.575 | 0.66 |

2.3 Effects on the Weekly Feed Intake and Total Food Utilization Ratio and Weekly Food Utilization Ratio of Rats See Tables 11 and 12 for the results. Compared to the solvent control group, there was no significant difference in the weekly feed intake, body weight gain, total feed intake, total food utilization ratio, weekly food utilization ratio or solvent control group of rats in each dose group (analysis of variance, rank sum test, P>0.05).

TABLE 11

Effects of Semen *Ziziphi Spinosae* Soft Capsules on the Weekly Feed Intake of Rats (X ± s)

| Gender | Dosage | Number of Rats (n) | Weekly Feed Intake | | | |
|---|---|---|---|---|---|---|
| | | | Week 1 | Week 2 | Week 3 | Week 4 |
| Female | Solvent control group | 10 | 90.7 ± 8.9 | 130.4 ± 10.4 | 133.9 ± 8.1 | 135.6 ± 5.7 |
| | Low-dose group | 10 | 88.1 ± 8.7 | 133.6 ± 10.1 | 123.9 ± 11.4 | 129.5 ± 8.2 |
| | Medium-dose group | 10 | 87.1 ± 12.7 | 131.4 ± 15.9 | 127.0 ± 12.8 | 129.4 ± 13.8 |
| | High-dose group | 10 | 93.3 ± 7.6 | 136.6 ± 10.1 | 127.5 ± 10.2 | 135.8 ± 8.6 |
| | F | | | 0.821 | 0.377 | 1.517 | 1.532 |
| | P | | | 0.491 | 0.77 | 0.227 | 0.223 |
| Male | Solvent control group | 10 | 97.2 ± 11.2 | 156.0 ± 8.32 | 185.4 ± 6.5 | 192. ± 8.3 |
| | Low-dose group | 10 | 100.3 ± 7.2 | 153.1 ± 12.4 | 185.1 ± 10.9 | 186.8 ± 16.6 |
| | Medium-dose group | 10 | 105.2 ± 14.0 | 161.3 ± 16.4 | 192.5 ± 17.0 | 190.4 ± 18.2 |
| | High-dose group | 10 | 98.4 ± 9.0 | 151.4 ± 14.0 | 185.9 ± 15.5 | 184.2 ± 12.7 |
| | F | | | 1.089 | 1.085 | 0.717 | 0.612 |
| | P | | | 0.366 | 0.367 | 0.548 | 0.611 |

TABLE 12

Effects of Semen Ziziphi Spinosae Soft Capsules on the Total Food Utilization Ratio and Weekly Food Utilization Ratio of Rats (X ± s)

| Gender | Dosage | Number of Rats (n) | Body Weight Gain (G) | Total Feed Intake (g) | Total Food Utilization Ratio (g) | Weekly Food Utilization Ratio (%) | | | |
|---|---|---|---|---|---|---|---|---|---|
| | | | | | | Week 1 | Week 2 | Week 3 | Week 4 |
| Female | Solvent control group | 10 | 143.2 ± 10.7 | 492.7 ± 23.6 | 29.1 ± 1.8 | 44.1 ± 6.0 | 33.6 ± 3.6 | 28.0 ± 3.8 | 15.5 ± 3.5 |
| | Low-dose group | 10 | 136.2 ± 7.4 | 475.1 ± 29.3 | 28.7 ± 1.3 | 47.2 ± 6.1 | 31.9 ± 4.7 | 25.3 ± 6.1 | 16.1 ± 5.4 |
| | Medium-dose group | 10 | 139.2 ± 15.2 | 475.0 ± 49.6 | 29.4 ± 1.9 | 51.2 ± 6.9 | 33.3 ± 3.9 | 26.2 ± 3.8 | 13.6 ± 3.0 |
| | High-dose group | 10 | 145.0 ± 11.2 | 493.2 ± 30.9 | 29.4 ± 2.2 | 47.3 ± 1.9 | 34.6 ± 3.2 | 34.6 ± 3.2 | 24.6 ± 2.5 |
| | F | | 1.186 | 2.855(H) | 0.327 | 2.733 | 0.805 | 1.185 | 0.581 |
| | P | | 0.329 | 0.415 | 0.806 | 0.058 | 0.5 | 0.329 | 0.631 |
| Male | Solvent control group | 10 | 235.7 ± 12.0 | 630.9 ± 28.2 | 37. ± 1.6 | 50.3 ± 4.3 | 40.7 ± 1.9 | 35.8 ± 2.1 | 5.8 ± 2.1 |
| | Low-dose group | 10 | 241.5 ± 21.5 | 625.2 ± 43.8 | 38.6 ± 1.6 | 52.7 ± 6.1 | 39.6 ± 3.0 | 36.0 ± 2.2 | 29.7 ± 2.8 |
| | Medium-dose group | 10 | 245.3 ± 23.1 | 649.4 ± 60.6 | 37.8 ± 1.9 | 48.4 ± 5.2 | 40.6 ± 1.6 | 6 ± 1.6 | 32.9 ± 2.6 |
| | High-dose group | 10 | 234.8 ± 19.2 | 620.0 ± 48.9 | 37.9 ± 1.7 | 51.2 ± 3.2 | 39.0 ± 3.1 | 35.1 ± 2.7 | 32.6 ± 3.4 |
| | F | | 0.660 | 0.743 | 0.942 | 1.389 | 1.111 | 0.211 | 2.235 |
| | P | | 0.582 | 0.533 | 0.431 | 0.262 | 0.357 | 0.888 | 0.101 |

2.4 Effects on the Hematology of Rats

See Table 13 for the results. The original data met the requirement for homogeneity of variance ($P>0.05$). Compared to the solvent control group, there was no significant difference in the hemoglobin, red blood cell count or white blood cell count of rats in each doe group (analysis of variance, $P>0.05$).

TABLE 13

Effects of *Semen Ziziphi* Spinosae Soft Capsules on the HB, RBC and WBC of Rats (X ± s)

| Gender | Dosage | Number of Rats (n) | WBC Count (×$10^9$/L) | RBC Count (×$10^9$/L) | Hemoglobin (g/L) |
|---|---|---|---|---|---|
| Female | Solvent control group | 10 | 5.98 ± 1.67 | 7.28 ± 0.25 | 150.9 ± 4.4 |
| | Low-dose group | 10 | 8.74 ± 2.86 | 7.22 ± 0.26 | 148.4 ± 4.2 |
| | Medium-dose group | 10 | 7.61 ± 1.86 | 7.18 ± 0.35 | 147.4 ± 5.3 |
| | High-dose group | 10 | 7.51 ± 2.69 | 7.21. ± 0.42 | 149.0 ± 5.8 |
| | F | | 2.371 | 0.161 | 0.878 |
| | P | | 0.087 | 0.922. | 0.462 |
| Male | Solvent control group | 10 | 12.00 ± 2.21 | 7.22 ± 0.29 | 149.2 ± 3.9 |
| | Low-dose group | 10 | 10.43 ± 2.57 | 7.39 ± 0.44 | 154.3 ± 6.9 |
| | Medium-dose group | 10 | 11.04 ± 1.37 | 7.18 ± 0.27 | 149.2 ± 4.1 |
| | High-dose group | 10 | 11.78 ± 3.32 | 7.39 ± 0.41 | 152.3 ± 6.8 |
| | F | | 0.861 | 0.721 | 2.006 |
| | P | | 0.470 | 0.546 | 0.131 |

2.5 Effects on the WBC of Rats

See Table 4 for the results. The numeric values were all within the historical control ranges of our laboratory and the original data met the requirement for homogeneity of variance ($P>0.05$). Compared to the solvent control group, there was no statistical difference in the leukocyte differential counts such as lymphocyte, monocyte and granulocytes of rats in each dose group (analysis of variance, $P>0.05$).

TABLE 14

Effects of Semen *Ziziphi Spinosae* Soft Capsules on the WBC of Rats (X ± s)

| Gender | Dosage | Number of Rats (n) | Lymphocyte (%) | Monocyte (%) | Granulocytes (%) |
|---|---|---|---|---|---|
| Female | Solvent control group | 10 | 71.7 ± 2.1 | 2.6 ± 0.5 | 25.7 ± 2.1 |
| | Low-dose group | 10 | 71.3 ± 3.8 | 2.6 ± 0.7 | 26.2 ± 3.3 |

TABLE 14-continued

Effects of Semen *Ziziphi Spinosae* Soft Capsules on the WBC of Rats (X ± s)

| Gender | Dosage | Number of Rats (n) | Lymphocyte (%) | Monocyte (%) | Granulocytes (%) |
|---|---|---|---|---|---|
| | Medium-dose group | 10 | 70.3 ± 4.1 | 2.7 ± 0.6 | 27.0 ± 3.8 |
| | High-dose group | 10 | 69.7 ± 3.1 | 2.4 ± 0.3 | 27.9 ± 3.1 |
| | F | | 0.728 | 0.506 | 0.930 |
| | P | | 0.542 | 0.681 | 0.436 |
| Male | Solvent control group | 10 | 70.8 ± 3.2 | 3.0 ± 0.6 | 26.2 ± 3.1 |
| | Low-dose group | 10 | 70.8 ± 3.9 | 3.2 ± 0.7 | 25.9 ± 3.8 |
| | Medium-dose group | 10 | 69.8 ± 4.8 | 3.8 ± 1.3 | 26.4 ± 4.9 |
| | High-dose group | 10 | 71.8 ± 4.2 | 3.1 ± 0.7 | 25.1 ± 4.0 |
| | F | | 0.395 | 1.419 | 0.206 |
| | P | | 0.757 | 0.253 | 0.892 |

2.6 Effects on the Blood Biochemistry of Rats

See Tables 15-16 for the results. The original data met the requirement for homogeneity of variance ($P>0.05$). Compared to the solvent control group, there was no significant difference in the serum alanine aminotransferase, aspartate aminotransferase, blood urea nitrogen, creatinine, total cholesterol, triglyceride, blood glucose, total protein, albumin, globulin or albumin/globulin ratio of rats in each dose group (analysis of variance, $P>0.05$).

TABLE 15

Effects of Semen *Ziziphi Spinosae* Soft Capsules on the Blood Biochemistry of Rats (I) (X ± s)

| Gender | Dosage | Number of Rats (n) | ALT (U/L) | Aspartate aminotransferase (U/L) | Blood urea nitrogen (mmmol/L) | Creatinine (mmol/L) | Triglyceride (mmmol/L) | Total cholesterol (mmmol/L) |
|---|---|---|---|---|---|---|---|---|
| Female | Solvent control group | 10 | 46.9 ± 9.3 | 275. ± 59.6 | 6.69 ± 1.02 | 64.9 ± 3.2 | 0.49 ± 0.09 | 1.98 ± 0.30 |
| | Low-dose group | 10 | 48.8 ± 10.8 | 282.4 ± 77.4 | 6.72 ± 0.99 | 63.8 ± 2.7 | 0.63 ± 2.7 | 1.71 ± 0.30 |
| | Medium-dose group | 10 | 47.2 ± 7.4 | 286.2 ± 32.6 | 6.97 ± 1.13 | 64.4 ± 3.3 | 0.64 ± 1.337 | 1.88 ± 0.31 |
| | High-dose group | 10 | 52.1 ± 8.1 | 298.9 ± 67.9 | 7.43 ± 1.44 | 66.3 ± 4.1 | 0.56 ± 0.16 | 1.75 ± 0.37 |
| | F | | 0.702 | 0.263 | 0.885 | 1.005 | 2.584 | 1.470 |
| | P | | 0.557 | 0.852 | 0.458 | 0.402 | 0.068 | 0.239 |
| Male | Solvent control group | 10 | 46.4 ± 7.6 | 264.1 ± 65.8 | 5.84 ± 0.94 | 60.3 ± 3.5 | 0.77 ± 0.17 | 1.60 ± 0.32 |
| | Low-dose group | 10 | 50.6 ± 9.5 | 287.6 ± 65.7 | 5.52 ± 0.39 | 60.6 ± 2.8 | 0.67 ± 0.16 | 1.45 ± 0.17 |
| | Medium-dose group | 10 | 47.4 ± 9.5 | 263.5 ± 44.4 | 5.08 ± 0.84 | 58.6 ± 4.5 | 0.74 ± 0.11 | 1.64 ± 0.34 |
| | High-dose group | 10 | 51.7 ± 10.4 | 299.7 ± 64.8 | 5.82 ± 0.87 | 61.4 ± 2.8 | 0.83 ± 0.19 | 1.61 ± 0.27 |
| | F | | 0.739 | 0.867 | 1.980 | 1.149 | 1.799 | 0.887 |
| | P | | 0.536 | 0.467 | 0.134 | 0.343 | 0.165 | 0.457 |

TABLE 16

Effects of Semen *Ziziphi Spinosae* Soft Capsules on the Blood Biochemistry of Rats (II) (X ± s)

| Gender | Dosage | Number of Rats (n) | total protein (g/L) | albumin (g/L) | globulin (g/L) | A/G Ratio | blood glucose (mmol/L) |
|---|---|---|---|---|---|---|---|
| Female | Solvent control group | 10 | 67.3 ± 2.4 | 34.2 ± 0.5 | 33.1 ± 2.3 | 1.04 ± 0.07 | 4.76 ± 0.42 |
| | Low-dose group | 10 | 66.2 ± 1.5 | 34.3 ± 0.8 | 31.9 ± 1.2 | 1.08 ± 0.05 | 4.45 ± 0.63 |
| | Medium-dose group | 10 | 66.9 ± 2.2 | 34.9 ± 1.1 | 33.0 ± 1.6 | 1.03 ± 0.05 | 4.33 ± 0.59 |
| | High-dose group | 10 | 68.6 ± 2.1 | 34.6 ± 0.8 | 34.0 ± 1.5 | 1.02 ± 0.03 | 4.50 ± 0.55 |
| | F | | 2.273 | 1.212 | 2.608 | 2.385 | 1.057 |
| | P | | 0.097 | 0.319 | 0.067 | 0.085 | 0.379 |

TABLE 16-continued

Effects of Semen Ziziphi Spinosae Soft Capsules on the Blood Biochemistry of Rats (II) (X ± s)

| Gender | Dosage | Number of Rats (n) | total protein (g/L) | albumin (g/L) | globulin (g/L) | A/G Ratio | blood glucose (mmol/L) |
|---|---|---|---|---|---|---|---|
| Male | Solvent control group | 10 | 65.4 ± 2.1 | 33.2 ± 1.1 | 32.3 ± 2.0 | 1.03 ± 0.08 | 4.87 ± 0.96 |
|  | Low-dose group | 10 | 63.3 ± 1.8 | 32.1 ± 0.6 | 31.2 ± 1.3 | 1.03 ± 0.03 | 4.50 ± 0.54 |
|  | Medium-dose group | 10 | 63.7 ± 2.0 | 32.3 ± 1.0 | 31.4 ± 1.5 | 1.03 ± 0.05 | 4.92 ± 0.62 |
|  | High-dose group | 10 | 64.9 ± 2.7 | 32.7 ± 0.9 | 32.2 ± 2.1 | 1.02 ± 0.06 | 4.49 ± 0.78 |
|  | F |  | 2.158 | 2.799 | 0.950 | 0.112 | 1.073 |
|  | P |  | 0.110 | 0.054 | 0.427 | 0.953 | 0.373 |

2.7 Effects on the Organ Weights and Organ/Body Weight Ratios of Rats

See Tables 17-18 for results. Except rank sum test was adopted for the kidney weight and ovary/body weight ratio of female rats and for the liver/body weight ratio of males that did not met the requirement for homogeneity of variance (P<0.05), the rest original data met the requirement for homogeneity of variance (P>0.05). Compared to the solvent control group, there was no significant difference in the weights of organs including liver, spleen, kidney and testis (ovary), or the fasting body weight or organ/body weight ratios [liver/body, spleen/body, kidney/body and testis (ovary)/body weight ratios] at the end of the experiment (analysis of variance and rank sum test, P>0.05).

TABLE 17

Effects of Semen Ziziphi Spinosae Soft Capsules on the Organ Weights of Rats (X ± s)

| Gender | Dosage | Number of Rats (n) | Liver Weight (g) | Kidney Weight (g) | Spleen Weight (g) | testis (ovary) (g) |
|---|---|---|---|---|---|---|
| Female | Solvent control group | 10 | 7.01 ± 0.50 | 1.78 ± 0.15 | 0.53 ± 0.09 | 0.13 ± 0.02 |
|  | Low-dose group | 10 | 7.02 ± 0.44 | 1.75 ± 0.10 | 0.52 ± 0.06 | 0.14 ± 0.02 |
|  | Medium-dose group | 10 | 7.09 ± 0.64 | 1.76 ± .023 | 0.52 ± 0.92 | 0.14 ± 0.04 |
|  | High-dose group | 10 | 7.18 ± 0.60 | 1.86 ± 0.12 | 0.52 ± 0.07 | 0.14 ± 0.01 |
|  | F |  | 0.201 | 2.593(H) | 0.021 | 0.641 |
|  | P |  | 0.895 | 0.459 | 0.996 | 0.594 |
| Male | Solvent control group | 10 | 9.82 ± 1.05 | 2.75 ± 0.18 | 0.76 ± 0.10 | 3.12 ± 0.14 |
|  | Low-dose group | 10 | 10.07 ± 0.82 | 2.80 ± 0.21 | 0.69 ± 0.11 | 3.29 ± 0.14 |
|  | Medium-dose group | 10 | 10.50 ± 1.10 | 2.83 ± 0.27 | 0.80 ± 0.20 | 3.07 ± 0.28 |
|  | High-dose group | 10 | 9.85 ± 1.13 | 2.64 ± 0.29 | 0.74 ± 0.13 | 3.10 ± 0.20 |
|  | F |  | 0.922 | 1.135 | 1.186 | 2.578 |
|  | P |  | 0.440 | 0.348 | 0.329 | 0.069 |

TABLE 18

Effects of Semen Ziziphi Spinosae Soft Capsules on the Organ/Body Weight Ratios of Rats (X ± s)

| Gender | Dosage | Number of Rats (n) | End-of experiment Fasting Body Weight (g) | Liver/ Body (%) | Kidney/ Body (%) | Spleen/ Body (%) | Testis (Ovary)/ Body (%) |
|---|---|---|---|---|---|---|---|
| Female | Solvent control group | 10 | 196.4 ± 10.1 | 3.57 ± 0.18 | 0.91 ± 0.06 | 0.27 ± 0.05 | 0.07 ± 0.01 |
|  | Low-dose group | 10 | 189.6 ± 11.1 | 3.70 ± 0.11 | 0.92 ± 0.06 | 0.28 ± 0.03 | 0.08 ± 0.01 |
|  | Medium-dose group | 10 | 190.1 ± 13.9 | 3.73 ± 0.17 | 0.93 ± 0.09 | 0.28 ± 0.04 | 0.07 ± 0.03 |
|  | High-dose group | 10 | 191.8 ± 11.3 | 3.74 ± 0.19 | 0.97 ± 0.05 | 0.27 ± 0.04 | 0.07 ± 0.01 |
|  | F |  |  | 0.699 | 2.221 | 1.604 | 0.116 | 6.065(H) |
|  | P |  |  | 0.599 | 0.102 | 0.205 | 0.950 | 0.108 |
| Male | Solvent control group | 10 | 280.8 ± 13.3 | 3.50 ± 0.34 | 0.98 ± 0.07 | 0.27 ± 0.03 | 1.11 ± 0.06 |
|  | Low-dose group | 10 | 282.2 ± 19.3 | 3.57 ± 0.15 | 0.99 ± 0.06 | 0.24 ± 0.06 | 1.17 ± 0.08 |
|  | Medium-dose group | 10 | 288.1 ± 23.9 | 3.64 ± 0.15 | 0.98 ± 0.06 | 0.28 ± 0.08 | 1.07 ± 0.08 |
|  | High-dose group | 10 | 277.7 ± 21.5 | 3.54 ± 0.21 | 0.95 ± 0.06 | 0.26 ± 0.03 | 1.12 ± 0.09 |

TABLE 18-continued

Effects of Semen *Ziziphi Spinosae* Soft Capsules on the Organ/Body Weight Ratios of Rats (X ± s)

| Gender | Dosage | Number of Rats (n) | End-of experiment Fasting Body Weight (g) | Liver/ Body (%) | Kidney/ Body (%) | Spleen/ Body (%) | Testis (Ovary)/ Body (%) |
|---|---|---|---|---|---|---|---|
| | F | | 0.476 | 3.286(H) | 1.001 | 1.188 | 2.782 |
| | P | | 0.701 | 0.35 | 0.403 | 0.328 | 0.055 |

2.8 Histopathological Examination of Rats

At the end of the test, all the experimental rats were given gross examination and a total of 80 rats were dissected. According to the requirements in the *Technical Specification for Inspection and Evaluation of Health Food* 2003, histopathological examination was conducted on the major organs liver, kidneys, spleen, stomach, intestine, testes and ovaries of rats in the high-dose experiment group and solvent control group. The collected samples were fixed in 10% neutral formalin, paraffin-embedded and prepared into slides routinely. The slides were 2-4 microns in thickness, stained by HE and examined under a 200-400× light microscope. See Table 19 for the results.

TABLE 19

Summary of Histopathological Examination Observations

| | | Solvent Control | | High-dose group | |
|---|---|---|---|---|---|
| Organ | Pathological Change | Male n = 10 | Female n = 10 | Male n = 10 | Female n = 10 |
| Liver | Centrilobular venous congestion | 3 | 1 | 2 | 3 |
| | Cellular granular degeneration | 0 | 0 | 0 | 0 |
| | Cellular vacuolar degeneration | 2 | 3 | 1 | 2 |
| | Intralobular focal inflammatory cell infiltration | 3 | 2 | 1 | 3 |
| | Sporadic inflammatory cell infiltrations in the portal area | 2 | 1 | 1 | 2 |
| | Spotted and focal necrosis with inflammatory cell infiltration | 0 | 2 | 1 | 3 |
| Kidneys | Mild swelling of renal tubular epithelial cells | 0 | 2 | 0 | 2 |
| | Interstitial focal inflammatory cell infiltration | 1 | 1 | 2 | 0 |
| | Mild cortical interstitial vascular dilatation and congestion | 2 | 1 | 2 | 1 |
| | Renal tubular focal calcium salt deposition | 0 | 0 | 0 | 0 |
| Spleen | Mild sinusoid dilatation and congestion | 1 | 1 | 2 | 0 |
| | Central vascular lymphatic sheath thickening | 0 | 0 | 0 | 0 |
| | Splenic corpuscle atrophy | 0 | 0 | 0 | 0 |
| Gastrointestinal tract | Microvascular congestion of lamina propria | 0 | 0 | 0 | 0 |
| | Submucosal vascular congestion | 0 | 0 | 0 | 0 |
| | Mucosal epithelium degeneration and necrosis | 0 | 0 | 0 | 0 |
| | Inflammatory cell aggregation of lamina propria | 0 | 0 | 0 | 0 |
| Testis | Spermatogenic epithelial cells reduced | 0 | 0 | 0 | 0 |
| | Seminiferous tubule atrophy | 0 | 0 | 0 | 0 |
| | Interstitial cell hyperplasia | 0 | 0 | 0 | 0 |
| Ovary | Ovarian cyst | 0 | 0 | 0 | 0 |
| | Ovarian hemorrhage | 0 | 0 | 0 | 0 |
| | Interstitial cell hyperplasia | 0 | 0 | 0 | 0 |

The above experimental results showed: In the 30-day Semen Ziziphi Spinosae soft capsules feeding test, no noticeable toxicity was observed in the outcome measures of the three dose groups.

Embodiment 10 Acute Toxicity Test

1 Sample character and treatment: Take the content of Semen Ziziphi Spinosae soft capsules, which is a brown liquid. Storage condition: Seal and store in a cool and dry place. The recommended human dose of the product is 1.0 g/60 kg/day. The test samples were aseptically packaged samples provided by the manufacturer. In the experiment, the samples were prepared into test solutions at different concentrations by using edible soybean oil or OMSO as the solvent.

2 Experimental animal and testing conditions: The experimental ICR mice and SD rats were provided by Zhejiang Laboratory Animal Center with the Laboratory Animal Production License No. SCXK(ZHE)2014-0001, at SPF grade. The feed for the experimental animals were provided by Zhejiang Laboratory Animal Center, which follows the standard GB14924.1-2001. Testing environment conditions:

Laboratory Animal Usage License No. SYXK(ZHE)2013-0190, barrier environment, range of temperature 20-24° C., and range of relative humidity 50-70%. Before the test, the experimental animals were acclimatized in the animal room environment for 3 days. Ames test was done in the specialized laboratory according to sterile operating procedures, the cleanliness of this laboratory reached local class 1000, the range of temperature was 20-25° C. and the range of relative humidity was 40-70%.

3 Experimental Methods:

3.1 Acute Oral Toxicity Test in Rats:

3.1.1 Experimental animal: SD rats, at SPF grade, 180-220 g in weight.

3.1.2 Dosage and administration: The experiment adopted the maximum tolerated dose method and set a dose group (36.0 g sample per 1 kg body weight). Before exposure, the rats were fasted overnight without water deprivation. 20 animals, including 10 males and 10 females, were orally given the investigational product via intragastric gavage: Right before the test, 90.0 g sample was taken and prepared into 0.9 g/mL (the maximum IG concentration) by adding edible soybean oil to 100 mL. The animals were given intragastric gavage twice (once every 4 h) according to 20 mL/kg body weight.

3.1.3 Outcome measures: After exposure, the rats' general state, toxicity symptom and death profile were observed for two weeks.

3.2 Acute Oral Toxicity Test in Mice:

3.2.1 Experimental animal: ICR mice, at SPF grade, 18-22 g.

3.2.2 Dosage and administration: The experiment adopted the maximum tolerated dose method and set a dose group (36.0 g sample per 1 kg body weight). Before exposure, the rats were fasted overnight without water deprivation. 20 animals, including 10 males and 10 females, were orally given the investigational product via intragastric gavage: Right before the test, 90.0 g sample was taken and prepared into 0.9 g/mL (the maximum IG concentration) by adding edible soybean oil to 100 mL. The animals were given intragastric gavage twice (once every 4 h) according to 20 mL/kg body weight.

3.2.3 Outcome measures: After exposure, the rats' general state, toxicity symptom and death profile were observed for two weeks.

3.3 Ames Test:

3.3.1 Test strains: Histidine auxotrophic mutants of *Salmonella typhimurium* $TA_{97}$, $TA_{98}$, $Ta_{100}$ and $TA_{102}$ were selected, which were provided by the Department of Toxicology, Shanghai Municipal Center for Disease Control & Prevention and preserved by our department. Biologically identified and qualified strains were tested.

3.3.2 Metabolic activation system ($S_9$): $S_9$ is the liver homogenate supernatant from polychlorinated biphenyl-induced SD rats and is confirmed to be biologically active by 2-AF and 1,8-dihydroxyanthraquinone tests. 10% $S_9$ mix was prepared according to the formula recommended in the *Technical Specification for Inspection and Evaluation of Health Food*.

3.3.3 Dose selection: The test adopted the plate incorporation method. 5000 μg/dish was selected as the maximum dose. 1.0 g sample was weighed and added with DMSO to 20 mL, blended well and prepared into 50,000 μg/mL solutions, which were diluted to 10,000, 2,000, 400 and 80 μg/mL successively with DMSO by 5-fold. The diluted solutions at different concentrations were given moist-heat sterilization at 121° C. for 20 min and then used in the test. During the test, each petri dish was added with 0.1 mL, i.e. 5,000, 1,000, 200, 40 and 8 μg/dish respectively for the doses. In the meantime, blank control group, solvent control group (DMSO) and positive control group were set and for each type of strain, three parallel dishes were set for each test concentration and tested with and without $S_9$. The test was repeated once.

3.3.4 Observation index: The reverse mutation colony number of each strain in the culture medium was directly counted.

3.4 Mouse Bone Marrow Cell Micronucleus Test:

3.4.1 Experimental animal: ICR mice, at SPF grade, 25-30 g.

3.4.2 Dosage and administration: According to the acute oral toxicity results of mice, three dose groups (2.5, 5.0 and 10.0 g/kg body weight) were set, together with one solvent control group (edible soybean) and one positive control group (cyclophosphamide 60 mg/kg body weight), with 10 mice (5 males and 5 females) in each group. The mice were given the samples every 24 h. 2.5, 5.0 and 10.0 g samples were weighed separately and prepared into 0.125, 0.25 and 0.50 g/mL by adding soybean oil right before the test. The animals were given intragastric gavage according to 20 mL/kg body weight, once daily for consecutive two days. They were executed at 6 h after the last gavage of sample, with the sternal bone marrow taken, prepared into slides, fixed in methanol and stained with Giemsa.

3.4.3 Outcome measure: During the microscopy, 1,000 polychromatic erythrocytes (PCE) were counted for each animal to calculate the micronucleus rate (MN‰).

3.5 Mouse Sperm Malformation Test:

3.5.1 Experimental animal: ICR mice, at SPF grade, 25-30 g.

3.5.2 Dosage and administration: According to the acute oral toxicity results of mice, three dose groups (2.5, 5.0 and 10.0 g/kg body weight) were set and prepared with soybean oil right before use. In additional, solvent control (edible soybean oil) and positive control (mitomycin C 2.0 mg/kg body weight) groups were set, with 7 male mice in each group. For the three dose groups, 2.5, 5.0 and 10.0 g samples were weighed separately, added with edible soybean oil to 20 mL and prepared into 0.125, 0.25 and 0.50 g/mL respectively right before the test. The animals were given intragastric gavage according to 20 mL/kg body weight once daily for consecutive five days. At day 35 after the first gavage of sample, mice were executed by cervical spine dislocation, after which 5 mice were randomly selected, whose bilateral epididymides were taken, placed into a petri dish containing a proper amount of physiological saline, cut into pieces by eye scissors, given suction filtration with four-layer lens paper, directly smeared on the slides, dried naturally, fixed in methanol and then stained with 1% eosin.

3.5.3 Outcome measure: The morphology of sperm was examined under the high-power microscope and for each mouse, 1,000 intact sperm was examined to record the type and number of aberrant sperm and calculate the abnormal sperm rate (%).

4 Experimental Results 4.1 Acute Oral Toxicity Test in Rats

See Table 20 for the results. After exposure, none of the experimental rats showed any noticeable toxicity symptom or died. The maximum acute oral tolerated dose of the sample was higher than 36.0 g/kg body weight both in female and male rats.

TABLE 20

Results of Acute Oral Toxicity Test of Semen *Ziziphi Spinosae* Soft Capsules in Rats

| Gender | Dose Group (g/kg) | Number of Animals | Early Weight (g) X ± S | End Weight (g) X ± S | Number of Death (n) | Mortality (%) |
|---|---|---|---|---|---|---|
| Female | 36.0 | 10 | 191.9 ± 7.7 | 220.2 ± 12.6 | 0 | 0 |
| Male | 36.0 | 10 | 195.7 ± 10.5 | 293.8 ± 16.1 | 0 | 0 |

4.2 Acute Oral Toxicity Test in Mice:

See Table 21 for the results. After exposure, none of the experimental mice showed any noticeable toxicity symptom or died. The maximum acute oral tolerated dose of the sample was higher than 36.0 g/kg body weight both in female and male mice.

TABLE 21

Results of Acute Oral Toxicity Test of Semen *Ziziphi Spinosae* Soft Capsules in Mice

| Gender | Dose Group (g/kg) | Number of Animals | Early Weight (g) X ± S | End Weight (g) X ± S | Number of Death (n) | Mortality (%) |
|---|---|---|---|---|---|---|
| Female | 36.0 | 10 | 20.2 ± 0.7 | 30.1 ± 1.9 | 0 | 0 |
| Male | 36.0 | 10 | 20.1 ± 1.3 | 34.0 ± 1.3 | 0 | 0 |

4.3 Ames Test:

As shown by the results, none of the reverse mutation colony numbers in the presence and absence of $S_9$ for samples at different doses was over two times that of the blank control group or solvent control group, and there was no noticeable dose-response relationship between groups.

The result of the Ames test of this sample was negative.

4.4 Mouse Bone Marrow Cell Micronucleus Test:

See Table 22 for the micronucleus rates of each dose group and control groups. The ratio of immature erythrocytes to the total erythrocyte count of each group was not less than 20% those of the control groups, not suggesting bone marrow depression. Statistically analyzed by Poisson's test, there was no significant difference in the micronucleus rate between each dose group and the solvent control group (P>0.05) and the mouse micronucleus test of this sample was negative.

TABLE 22

Results of Mouse Bone Marrow Cell Micronucleus Test of Semen *Ziziphi Spinosae* Soft Capsules

| Gender | Dosage | Number of Rats | Number of Tested PCEs (n) | Number of Micronucleus-containing PCEs | Micronucleus-Cell Rate (‰) | P | PCE/RBC |
|---|---|---|---|---|---|---|---|
| Female | Solvent control edible soybean | 5 | 5000 | 5 | 1.0 ± 1.0 | / | 1.25 ± 0.13 |
| | 2.5 | 5 | 5000 | 6 | 1.2 ± 1.1 | 0.762 | 1.19 ± 0.11 |
| | 5.0 | 5 | 5000 | 4 | 0.8 ± 0.8 | 0.440 | 1.29 ± 0.34 |
| | 10.0 | 5 | 5000 | 4 | 0.8 ± 1.1 | 0.440 | 1.46 ± 0.49 |
| | Cyclophosphamide 60 mg/kg | 5 | 5000 | 123 | 24.6 ± 6.3 | <0.001 | 1.07 ± 0.13 |
| Male | Solvent control edible soybean | 5 | 5000 | 6 | 1.2 ± 0.8 | / | 1.31 ± 0.24 |
| | 2.5 | 5 | 5000 | 6 | 1.2 ± 1.3 | 0.606 | 1.43 ± 0.31 |
| | 5.0 | 5 | 5000 | 5 | 1.0 ± 1.0 | 0.715 | 1.43 ± 0.39 |
| | 10.0 | 5 | 5000 | 6 | 1.2 ± 0.8 | 0.606 | 1.29 ± 0.41 |
| | Cyclophosphamide 60 mg/kg | 5 | 5000 | 138 | 27.6 ± 10.4 | <0.001 | 1.21 ± 0.14 |

4.5 Mouse Sperm Malformation Test:

See Table 23 for the abnormal sperm rate of mice in each dose group and control groups. Statistically analyzed by the rank sum test, there was no significant difference in the abnormal sperm rate between each group and the negative or solvent control group (P>0.05). The mouse sperm malformation test of this sample was negative.

TABLE 23

Results of Mouse Sperm Malformation Test of Semen *Ziziphi Spinosae* Soft Capsules

| Group (g/kg) | Number of Rats (n) | Number of Sperm Tested(n) | Hook-free | Big head | Banana | Two-head/two-tail | Folded | Amorphous | Sub-total (n) | Abnormal Rate (%) |
|---|---|---|---|---|---|---|---|---|---|---|
| Solvent control | 5 | 5000 | 28 | 6 | 4 | 0 | 6 | 84 | 128 | 2.56 ± 0.85 |
| Investigational product 2.5 | 5 | 5000 | 38 | 7 | 3 | 4 | 2 | 101 | 155 | 3.10 ± 0.42 |
| Investigational product 5.0 | 5 | 5000 | 22 | 7 | 14 | 1 | 3 | 106 | 153 | 3.06 ± 0.58 |
| Investigational product 10.0 | 5 | 5000 | 20 | 17 | 9 | 2 | 6 | 115 | 169 | 3.38 ± 0.79 |
| Mitomycin C 2.0 mg/kg | 5 | 5000 | 113 | 5 | 23 | 10 | 24 | 119 | 294 | 5.88 ± 0.97# |
| H | | | | | | 3.547 | | | | |
| P | | | | | | 0.315 | | | | |

Compared to the negative control group, #P<0.01

As shown by the experimental results above, the maximum acute oral tolerated dose of Semen Ziziphi Spinosae soft capsules was higher than 36.0 g/kg body weight in both female and male rats and mice; The Ames test, mouse bone marrow cell micronucleus test and mouse sperm malformation test were all negative.

Embodiment 11 Semen Ziziphi Spinosae Oil Fingerprint Study

I. Experimental Materials and Reagents

Semen Ziziphi Spinosae Oil Sample 1 (Xi'an Xuhuang Bio-Tech Co., Ltd., Lot No. 20101017)

Semen Ziziphi Spinosae Oil Sample 2 (Semen Ziziphi Spinosae oil prepared in the Embodiment 5 of the present invention)

37-type FAME (fatty acid methyl alkane) mixed control product (Supelco Inc., USA No. N293876)

Methyl stearate control product (Sigma-Aldrich, Inc. No. S5376)

Methyl palmitate control product (Sigma-Aldrich, Inc. No. P5177)

Glyceryl behenate control product (Sigma-Aldrich, Inc. No. B3271)

Methyl arachidate control product (Sigma-Aldrich, Inc. No. A3881)

Methyl arachidonate control product (Sigma-Aldrich, Inc. No. E6885)

a-methyl linolenate control product (China National Institute for the Control of Pharmaceutical and Biological Products No. 111624-200301)

Methyl oleate control product (Aladdin company No. 47981)

Methyl linoleate control product (Aladdin company No. M102818)

Sodium hydroxide, absolute methanol, boron trifluoride-methanol solution (mass fraction 12%-15%), sodium chloride, sodium sulfate anhydrous, purified water, hydrogen, nitrogen, isooctane, etc.

II. Experimental Instruments

METTLER TOLEDO AL204 electronic balance [METTLER TOLEDO Instruments (Shanghai) Co., Ltd.]

PerKinElmer Clarus 680 PerkinElmer Inc.

SP™-2560 Supelco quartz capillary column (100 m×0.25 mm, 0.25 μm)

Agilent J&W Scientific DB-WAX quartz capillary column (30 m×0.32 mm, 0.25 μm)

PE Elite-WAX (30 m×0.32 mm, 0.25 um)

III. Test Method

1. Preparation of Control Solutions 1.1 Preparation of 37-type FAME (fatty acid methyl alkane) mixed control product: Take 1 ampoule of 37-type FAME mixed control product (labelled amount 25 mg), dissolve the product by adding 1 mL isooctane and get the mixed standard solution at the concentration of 25 mg/mL.

1.2 Preparation of methyl stearate control solution: Precisely weigh 11.59 mg of methyl stearate control product, dissolve it and fix the volume by adding 10 mL isooctane, and get the methyl stearate control solution at the concentration of 1.159 mg/mL.

1.3 Preparation of methyl palmitate control solution: Precisely weigh 12.70 mg of methyl palmitate control product, dissolve it and fix the volume by adding 10 mL isooctane, and get the methyl palmitate control solution at the concentration of 1.270 mg/mL.

1.4 Preparation of glyceryl behenate control solution: Precisely weigh 12.31 mg of glyceryl behenate control product, dissolve it and fix the volume by adding 10 mL isooctane, and get the methyl behenate control solution at the concentration of 1.231 mg/mL.

1.5 Preparation of methyl arachidate control solution: Precisely weigh 13.60 mg of methyl arachidate control product, dissolve it and fix the volume by adding 10 mL isooctane, and get the methyl arachidate control solution at the concentration of 1.360 mg/mL.

1.6 Preparation of arachidonic acid control solution: Precisely weigh 61.89 mg of methyl arachidonate control product, dissolve it and fix the volume by adding 10 mL isooctane, and get the methyl arachidonate control solution at the concentration of 6.189 mg/mL.

1.7 Preparation of methyl linolenate control solution: Precisely weigh 141.38 mg of methyl linolenate control product, dissolve it and fix the volume by adding 10 mL isooctane, and get the methyl linolenate control solution at the concentration of 14.138 mg/mL.

1.8 Preparation of methyl oleate control solution: Precisely weigh 815.96 mg of methyl oleate control product, dissolve it and fix the volume by adding 50 mL isooctane, take 5 mL solution into a 10 mL volumetric flak, fix the volume by adding isooctane, and get the methyl oleate control solution at the concentration of 8.16 mg/mL.

1.9 Preparation of methyl linoleate control solution: Precisely weigh 386.75 mg of methyl linoleate control product, dissolve it and fix the volume by adding 25 mL isooctane, take 5 mL solution into a 10 mL volumetric flak, fix the volume by adding isooctane, and get the methyl linoleate control solution at the concentration of 7.735 mg/mL.

2 Preparation of Sodium Hydroxide-Methanol Solution

Weigh 20 g of sodium hydroxide, add 1 L of absolute methanol, and get the 0.5 mol/l sodium hydroxide-methanol solution by ultrasonic dissolution 3 Preparation of Test Solution Take 0.4 g of test sample, place into a 50 mL flask, add 6 mL of sodium hydroxide-methanol solution, and then connect with condenser water bath, and recirculate until the oil drops disappear, and slowly shake the flask every 30 sec to avoid solids formed by sodium hydroxide from being adhered onto the flask wall; recirculate 10 min, add 7 mL of boron trifluoride-methanol solution into the boiled solution through the top of the condenser using a pipette, boil for another 3 min, add 5 mL of isooctane into the boiling mixed solution through the top of the condenser, remove the condenser, take out the flask, add in 20 mL of sodium chloride solution immediately, plug the flask, shake the flask violently for 15 sec, transfer the mixed solution into a 150 mL separatory funnel, rinse the flask with 10 mL of isooctane solution twice (5 mL each time), merge the washing liquid into the separatory funnel, let the funnel stand still to stratify the solution, abandon the subnatant water liquid, place the supernatant isooctane solution into a 25 mL flask, fix the volume using isooctane, add a proper amount of sodium sulfate anhydrous to absorb the trace amount of water in the solution, shake the flask well and put aside for subsequent use.

4 Gas Chromatographic Conditions

GC: PerKinElmer Clarus 680

Chromatographic column: Agilent J&W Scientific DB-WAX quartz capillary column (30 mm×0.32 mm, 0.25 μm)

Temperature Programming:

| Heating Rate (° C./min) | Temperature (° C.) | Holding Time (min) |
|---|---|---|
|  | 150 | 5 |
| 2.5 | 230 | 5 |

$N_2$: Flow rate 1 mL/min,
Injector temperature: 270° C.,
Detector: 270° C.,
Splitting ratio: 1:50
Injection volume: 1 μL
Air:hydrogen=10:1.

5 Test Method

Precisely draw 1 μL standard solution and 1 μL test solution into the gas chromatograph and conduct the test.

IV. Experimental Results and Analysis

1 Study on the source of Semen Ziziphi Spinosae Oil

Figure 2:
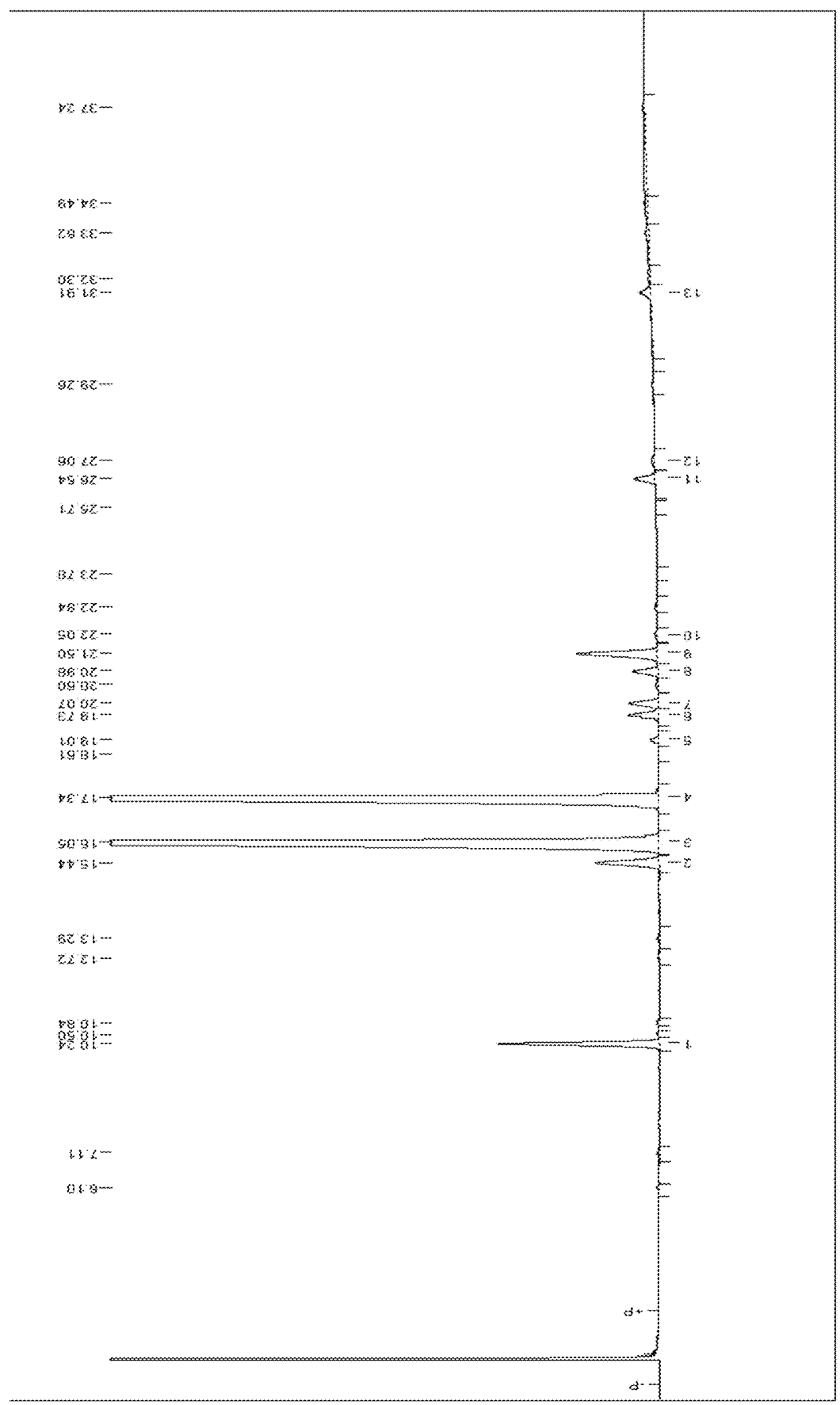
FIG. 2 Chromatogram of Semen Ziziphi Spinosae Oil Sample 2

See FIGS. 1 and 2 for the fingerprints of Semen Ziziphi Spinosae oil samples 1 and 2, respectively.

It can be seen from the chromatograms that, the two Semen Ziziphi Spinosae oil samples had an identical number of main chromatographic peaks (components), but differed in the content of each chromatographic peak (component), and the component contents of sample 2 were significantly higher than those of sample 1. As shown in the figures, 13 consensus chromatographic peaks were identified, which accounted for over 96% of the total peak area. Among them, the methyl oleate chromatographic peak (#3) was marked as s peak, with a relative peak area of 1 and a relative retention time of 1.

1.1 Study on the Chromatographic Column Types

Figure 3:
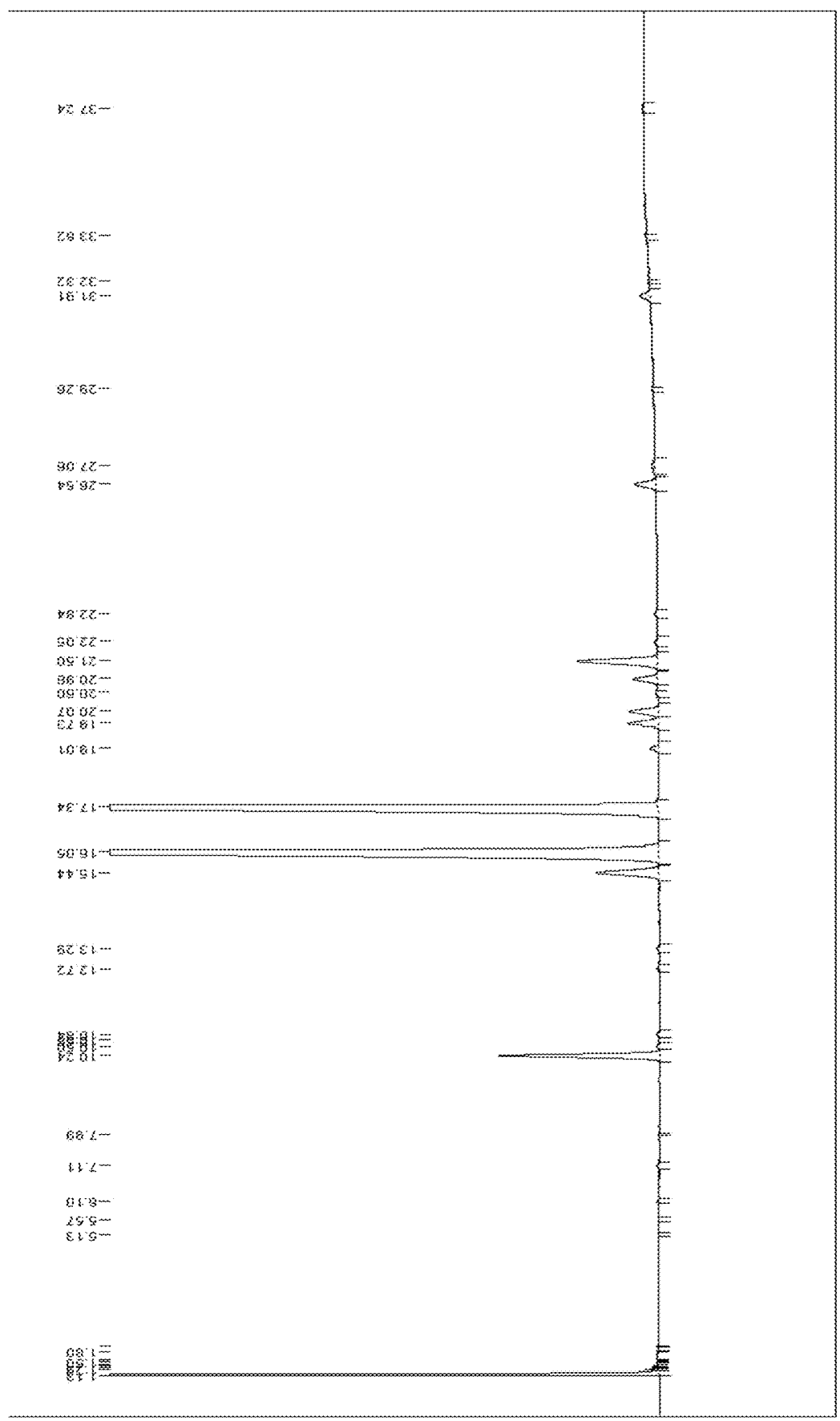
FIG. 3 Agilent GC Column Chromatogram
Figure 4:
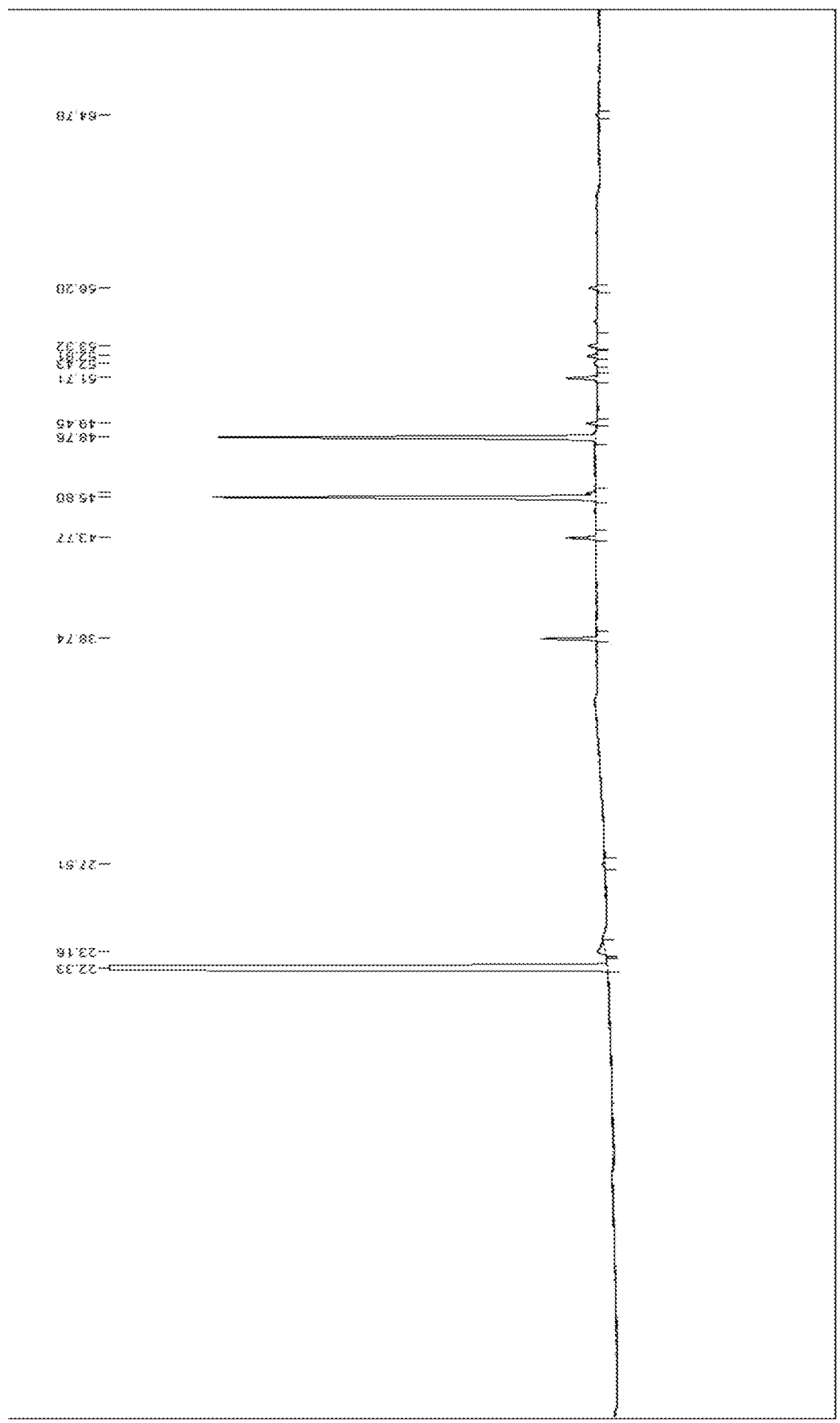
FIG. 4 Supelco GC Column Chromatogram
Figure 5:
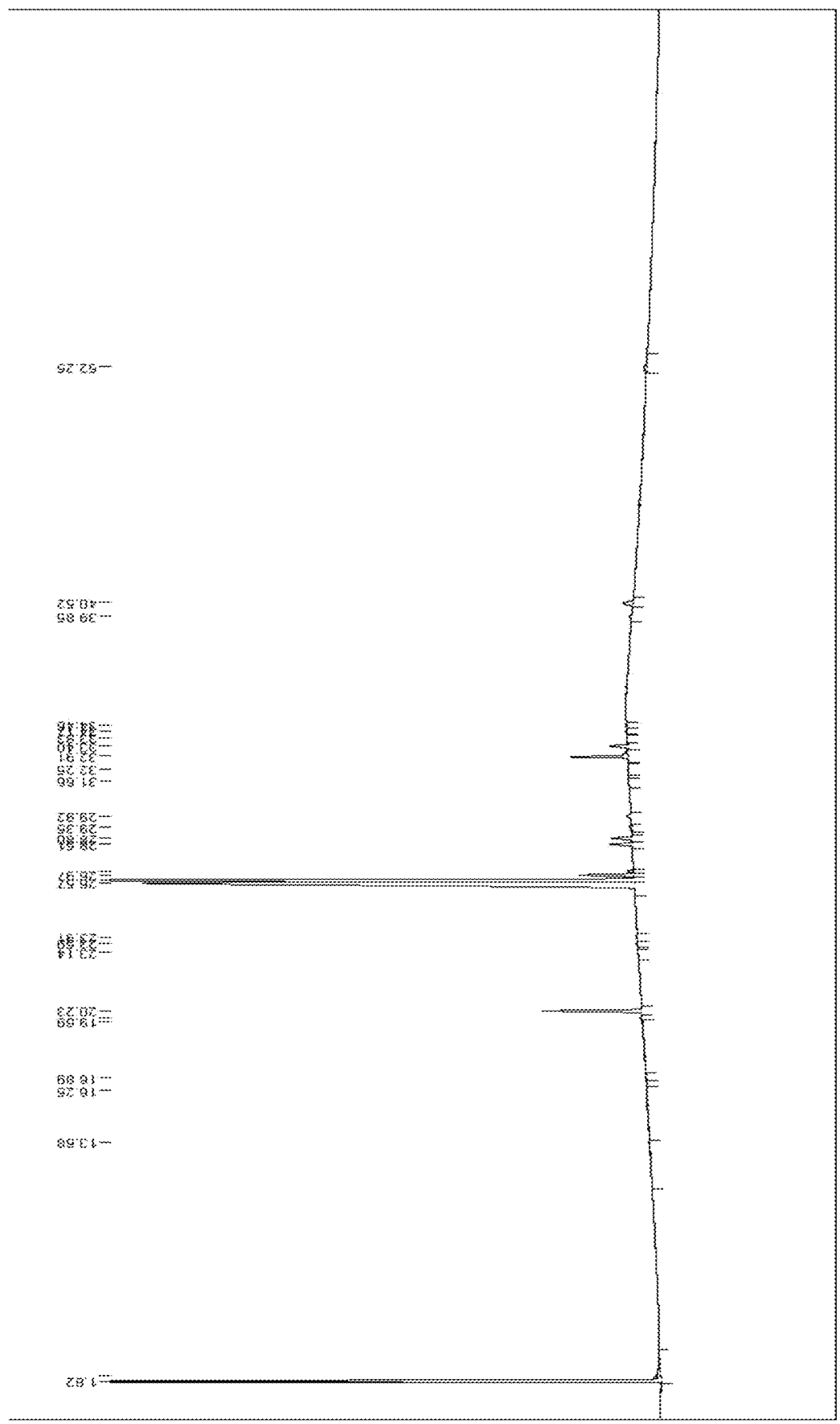
FIG. 5 PE GC Column Chromatogram

Three different brands and types including SP™-2560 Supelco quartz capillary column (100 m×0.25 mm, 0.25 μm), Agilent J&W Scientific DB-WAX quartz capillary column (30 m×0.32 mm, 0.25 μm) and PE Elite-WAX (30 m×0.32 mm, 0.25 μm) were compared in terms of the separation effect. See FIGS. 3-5 for the gas chromatograms of different chromatographic columns:

Analysis of results: It can be seen from the chromatograms that, when testing the sample, SP™-2560 Supelco quartz capillary column (100 m×0.25 mm, 0.25 μm) had the following problems: (1) The sample analysis time was too long and it took 75 min to analyze one sample when the nitrogen flow rate was 1 mL/min; as shown in the literature, the recommended flow rate for 100 m long chromatographic columns is usually 0.6-0.8 mL/min, in which case, the analysis time will be longer and if the nitrogen flow rate is excessively high, the column cap pressure will be excessively high and consequently damage the chromatographic column. (2) The loading capacity of SP™-2560 Supelco quartz capillary column (100 m×0.25 mm, 0.25 μm) was too small and under the same conditions, its chromatographic peak area was only 40% of that of Agilent GC chromatographic column. As found by consulting related literature, the loading capacity of chromatographic column is affected by its inner diameter and inner coating thickness. The inner diameter and inner coating thickness of SP™-2560 Supelco quartz capillary column (100 m×0.25 mm, 0.25 μm) are 0.25 mm and 0.25 μm respectively, both relatively small, and subsequently its loading capacity is relatively low. As shown in the literature, Supelco chromatographic column is relatively useful for separating fatty acid isomers of complex vegetable oil, and we have also found by detecting the separation of 37-type fatty acid control product that, Supelco chromatographic column was indeed superior to Agilent chromatographic column in separating isomers; however, if the tested vegetable oil did not contain any fatty acid isomers or only contained a small amount of isomers, Agilent J&W Scientific DB-WAX quartz capillary column (30 m×0.32 mm, 0.25 μm) is preferred, with the analysis time (efficiency of analysis) taken into account. PE Elite-WAX (30 m×0.32 mm, 0.25 μm) chromatographic column had a poor separation effect and failed to achieve baseline separation of chromatographic peaks. As found by consulting literature, PE Elite-WAX (30 m×0.32 mm, 0.25 μm) gas chromatographic column is usually suitable for separating solvents, freon, fluorinated hydrocarbon, alcohols, ketones, silicane and ethylene glycol, but not suitable for the separation of fatty acid components. For the separation of main chromatographic peaks of vegetable oil, Agilent J&W Scientific DB-WAX quartz capillary column (30 m×0.32 mm, 0.25 μm) can basically meet the separation requirements and therefore Agilent J&W Scientific DB-WAX quartz capillary column (30 m×0.32 mm, 0.25 μm) was eventually selected.

1.2 Study on the Splitting Ratio

The Agilent J&W Scientific DB-WAX quartz capillary column (30 m×0.32 mm, 0.25 μm) was adopted to investigate the chromatographic separation effects of four different splitting ratios including 10:1, 30:1, 50:1 and 100:1 and the results showed that, the splitting ratio of 10:1 was too big and failed to achieve baseline separation due to overloaded injection volume; the splitting ratio of 100:1 led to an inadequate injection volume and subsequently the chromatographic peak area was too small; both the splitting ratios of 30:1 and 50:1 were appropriate, and the splitting ratio was eventually determined as 50:1.

1.3 Study on the Flow Rate

The Agilent J&W Scientific DB-WAX quartz capillary column (30 m×0.32 mm, 0.25 μm) was adopted to investigate the chromatographic separation effects at different nitrogen flow rates including 1.0 mL/min, 1.3 mL/min and 1.5 mL/min and the results showed that, the nitrogen flow rate had a relatively small effect on the shape of chromatographic peaks and but a relatively big effect on their retention time. The bigger the flow rate, the shorter the retention time of each chromatographic peak was. As considered comprehensively, the flow rate was eventually determined as 1.0 mL/min.

1.4 37-Type FAME Control Product

Figure 6:
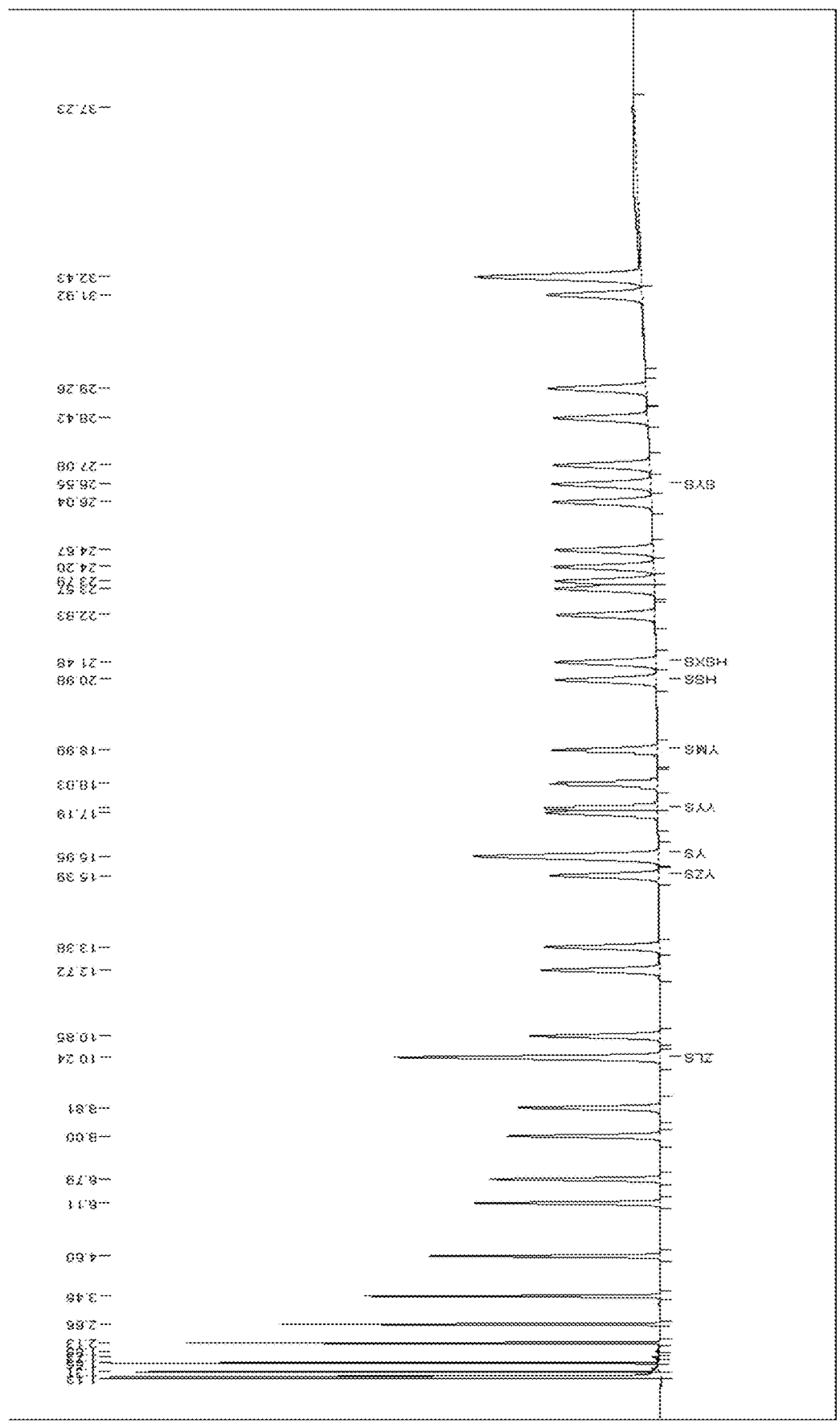
FIG. 6 Chromatogram of 37-type FAME (Fatty Acid Methyl Alkane) Mixed Control Product FIG. 7 Chromatogram of Solvent Blank Control FIG. 8 Chromatogram of Methyl Stearate Control Product FIG. 9 Chromatogram of Methyl Palmitate Control Product FIG. 10 Chromatogram of Methyl Behenate Control Product FIG. 11 Chromatogram of Methyl Arachidate Control Product FIG. 12 Chromatogram of Methyl Arachidonate Control Product FIG. 13 Chromatogram of Methyl Linolenate Control Product FIG. 14 Chromatogram of Methyl Oleate Control Product FIG. 15 Chromatogram of Methyl Linoleate Control Product FIG. 16 Fingerprint of the Fatty Acid Components of Semen Ziziphi Spinosae Oil FIG. 17 Fingerprint of the Fatty Acid Components of Semen Ziziphi Spinosae Oil (Scale-up)

The 37-type FAME control product prepared above was taken and tested according to the above GC conditions. See FIG. 6 for the chromatogram.

1.5 Blank Control

Figure 7:
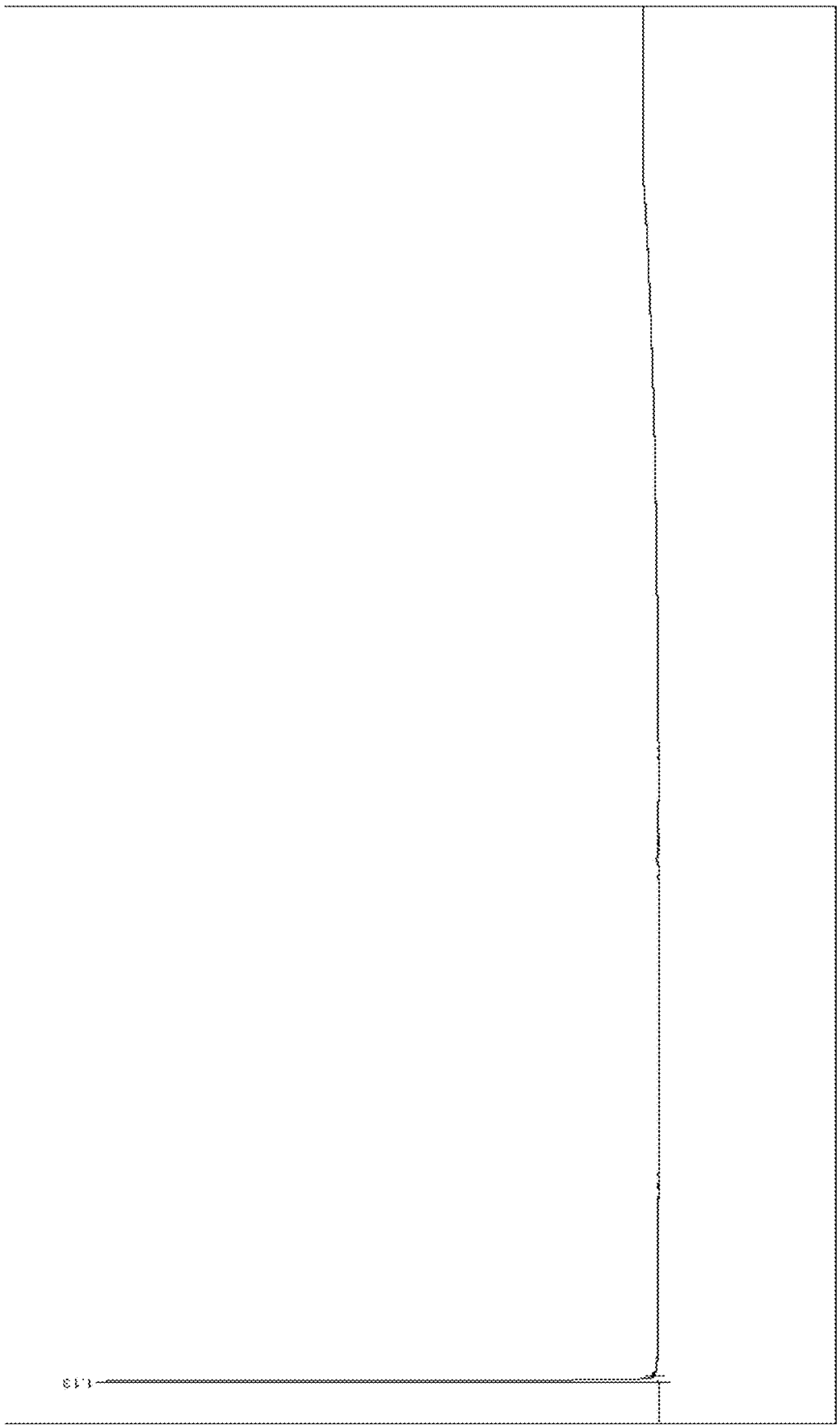
Figure 8:
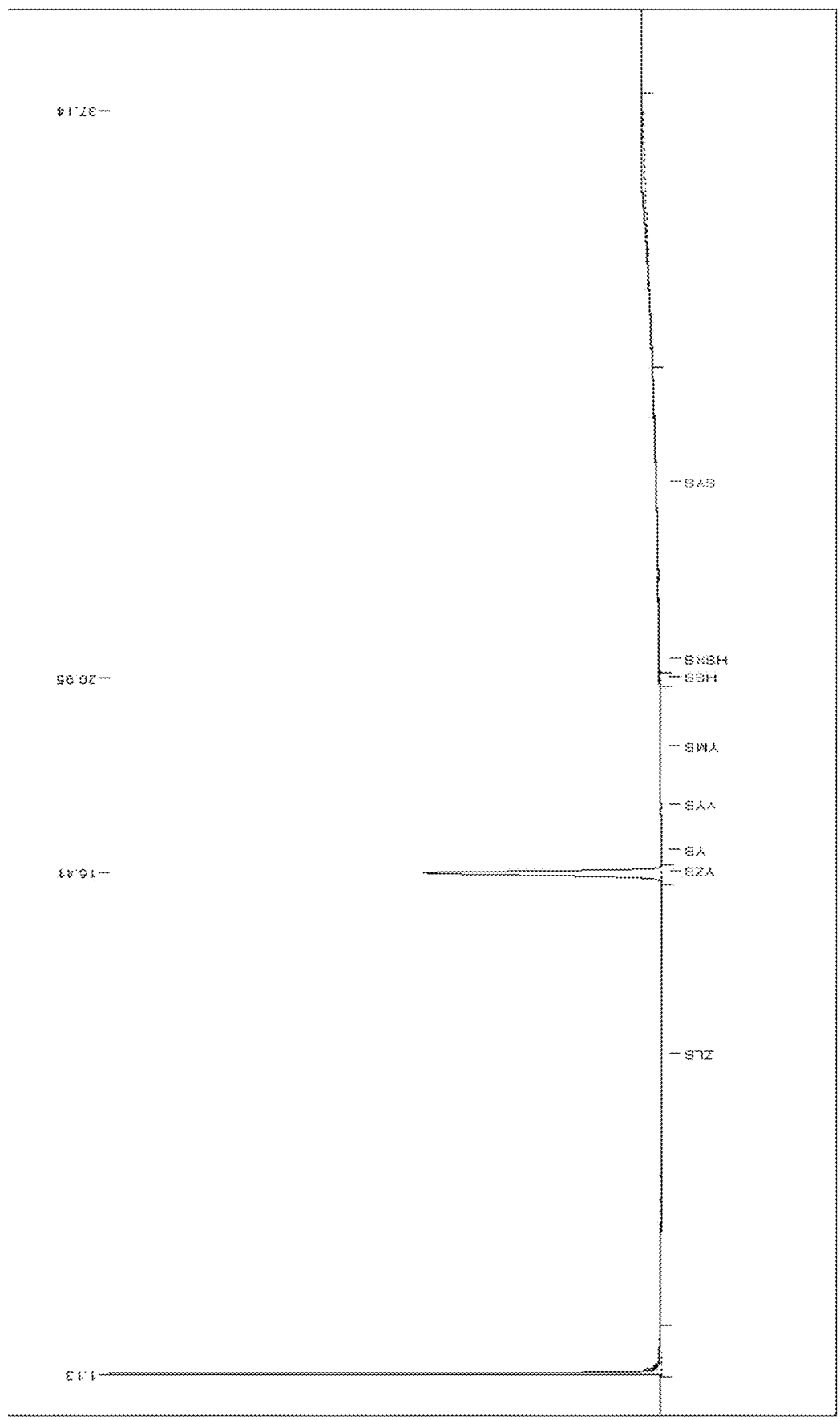
Figure 9:
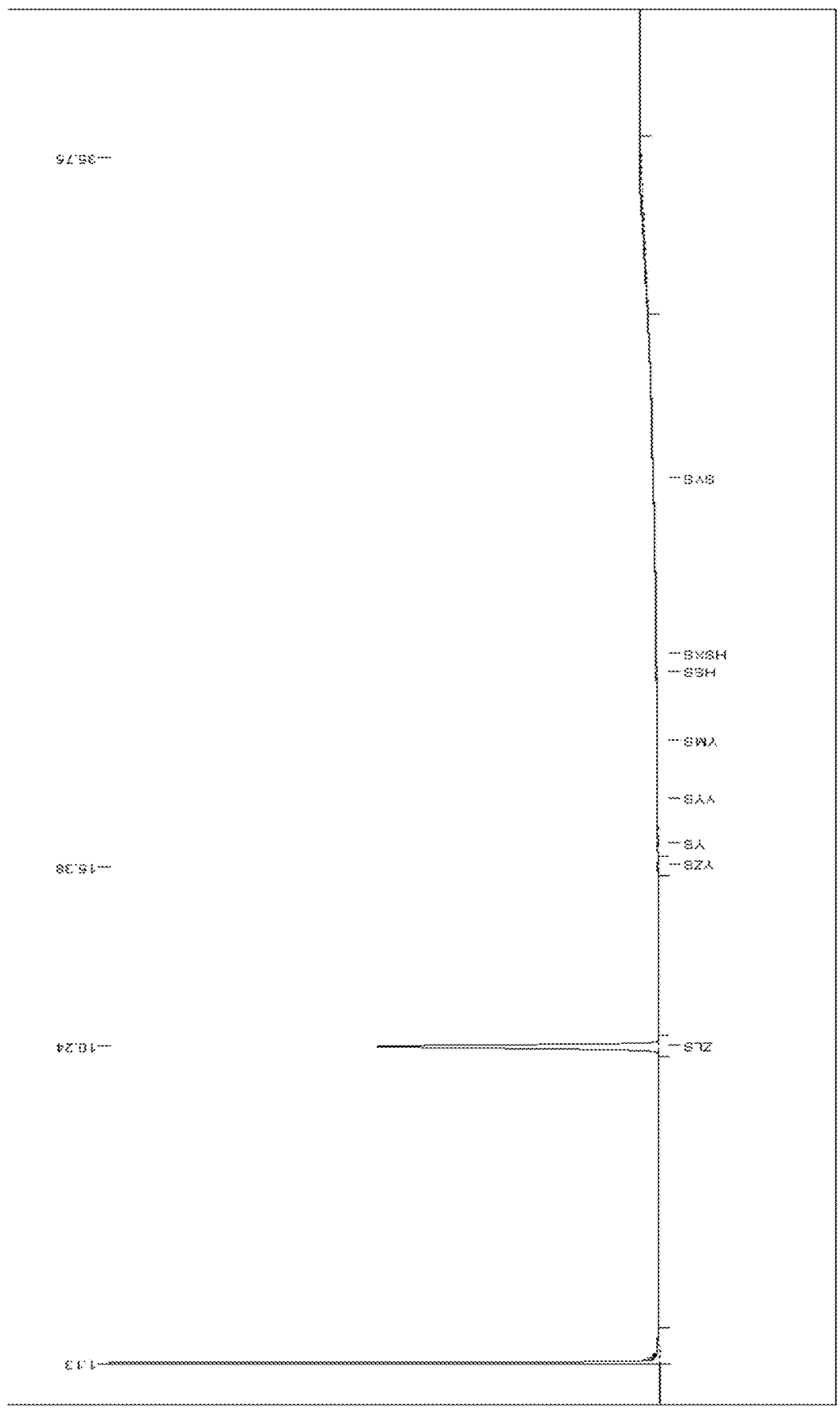
Figure 10:
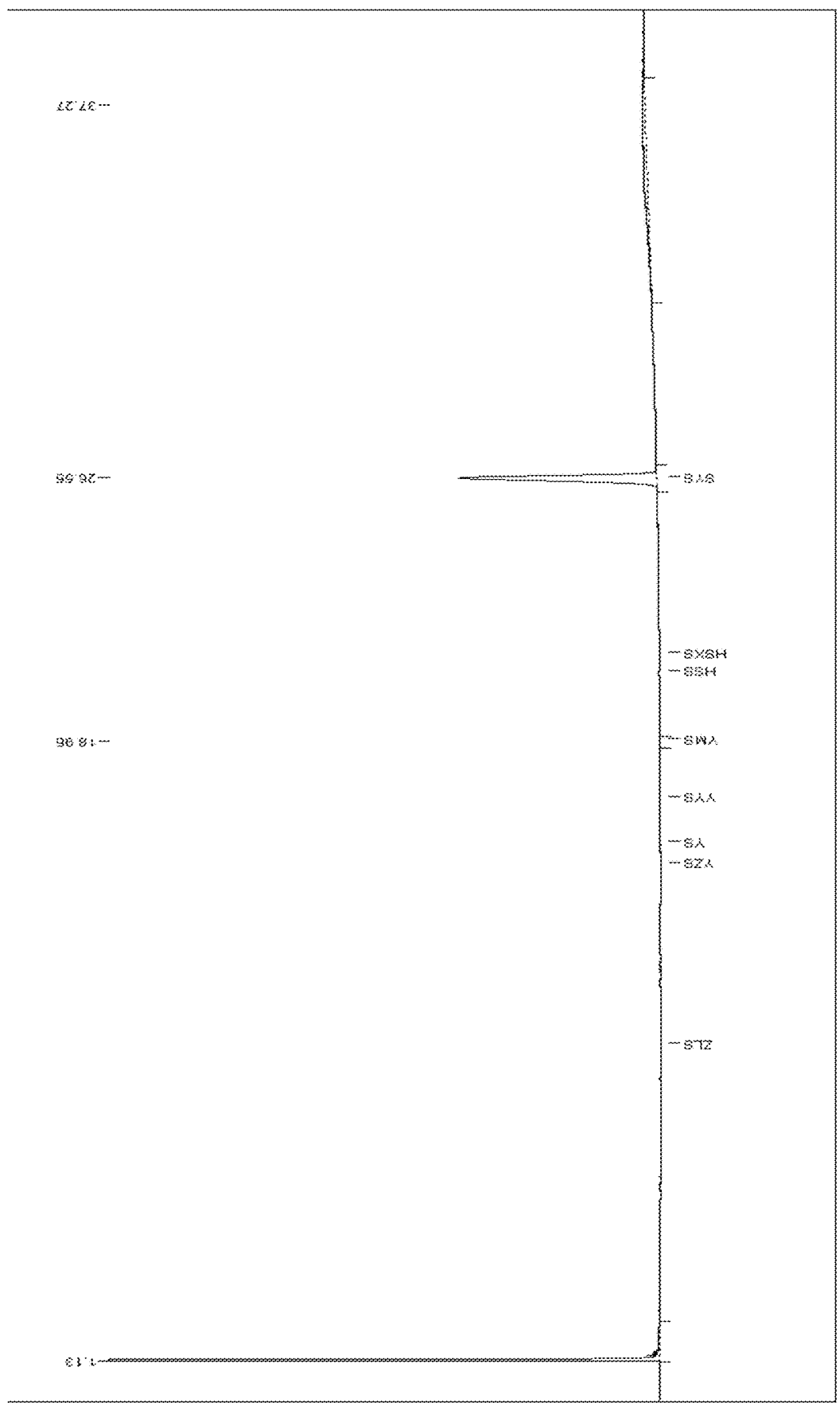
Figure 11:
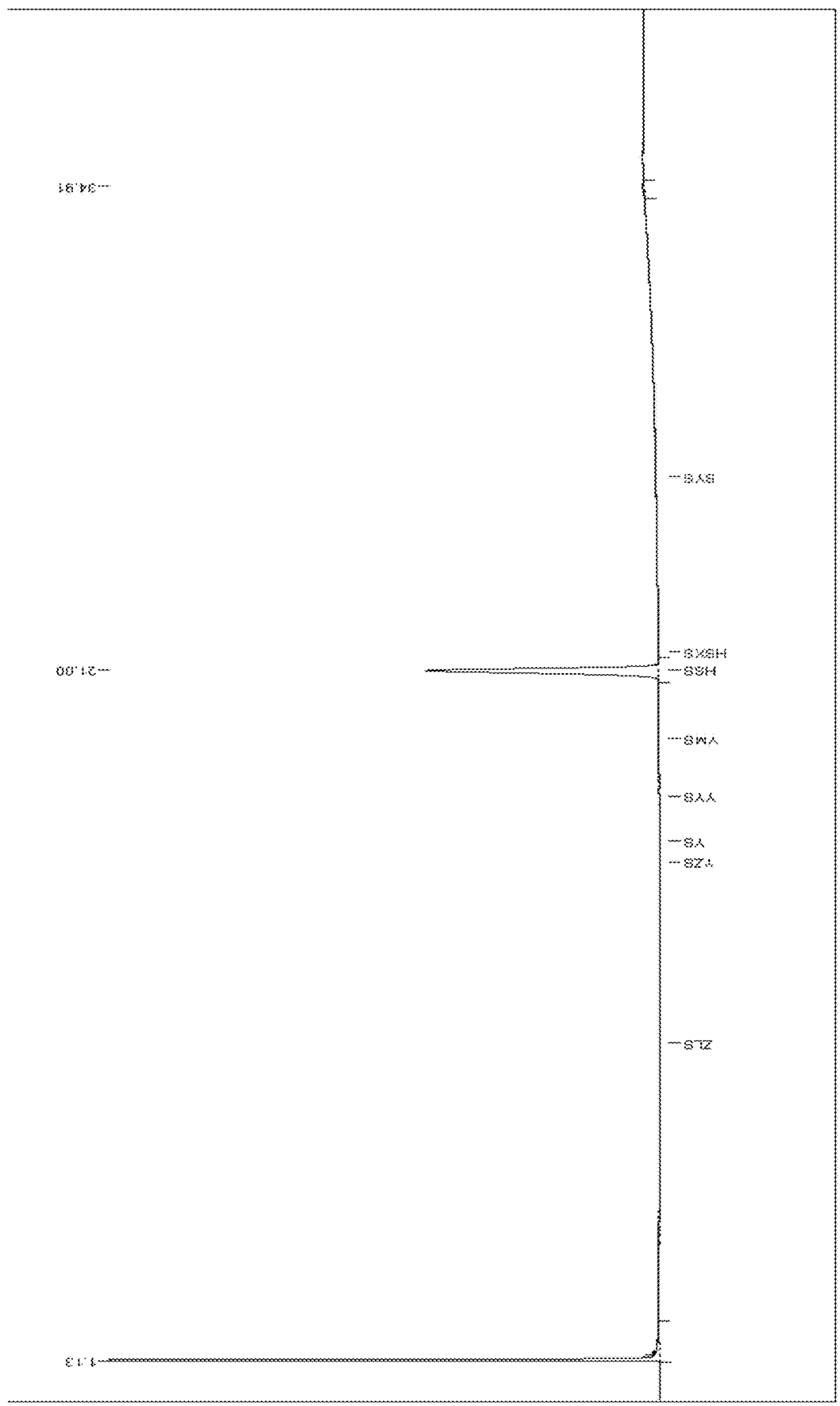
Figure 12:
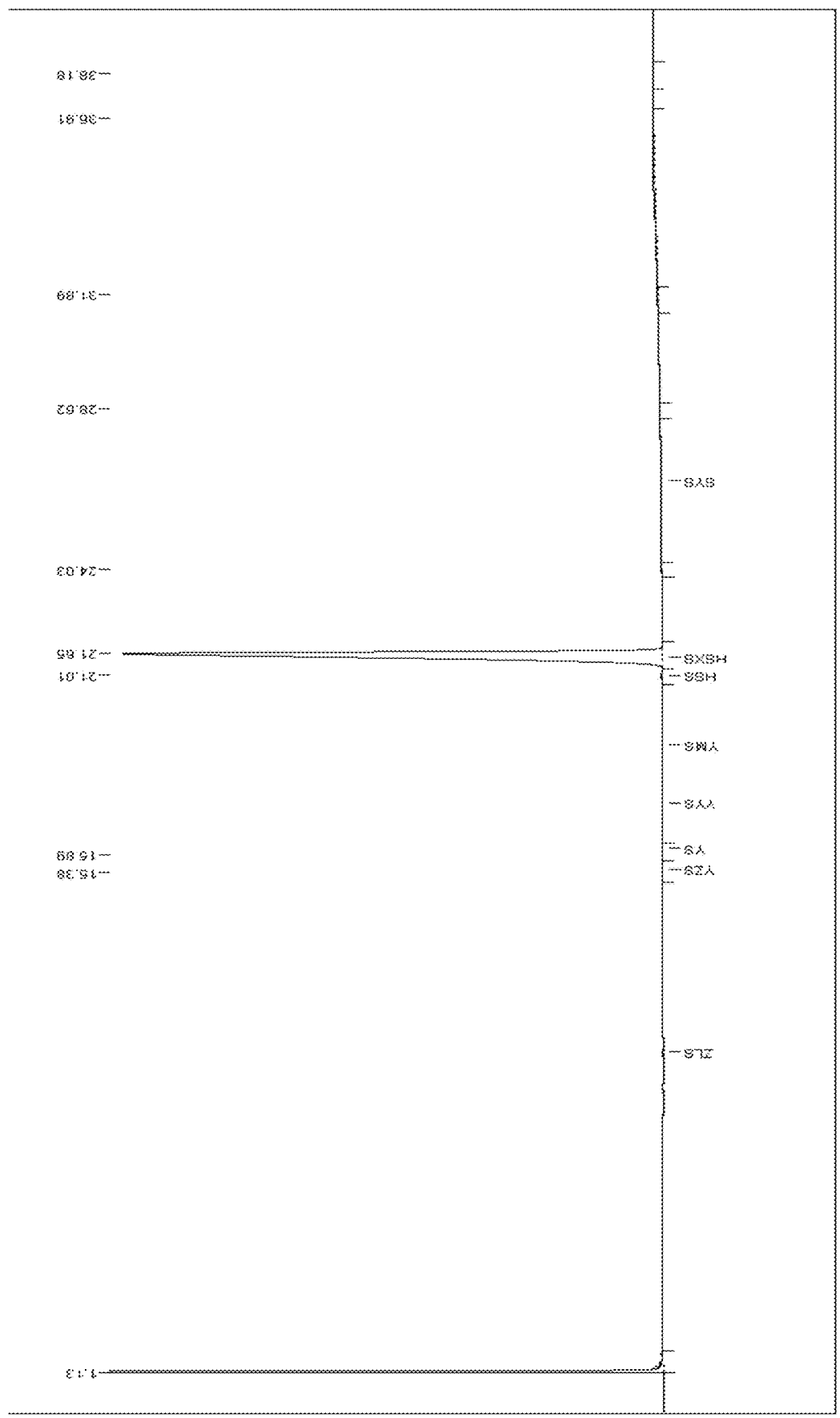
Figure 13:
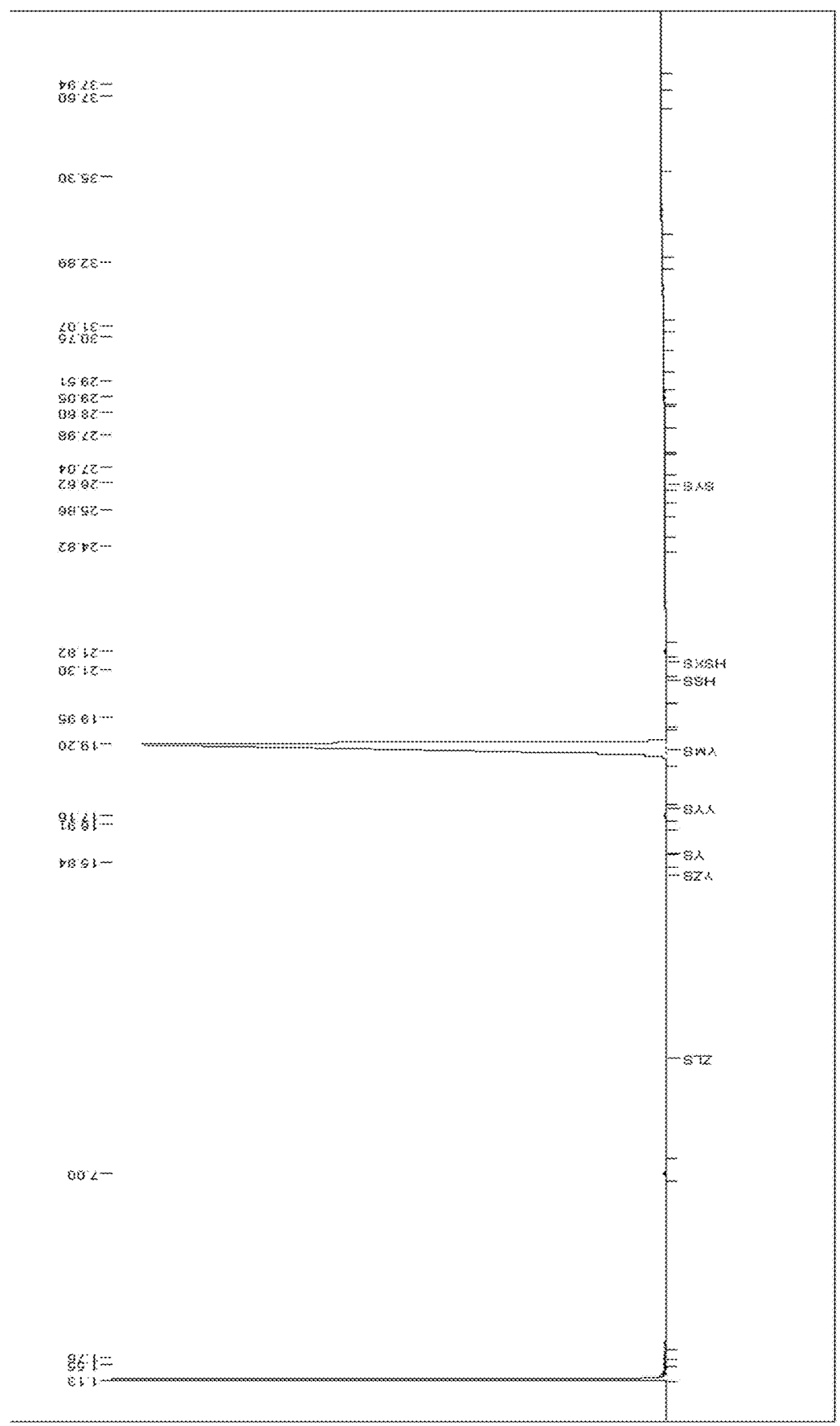
Figure 14:
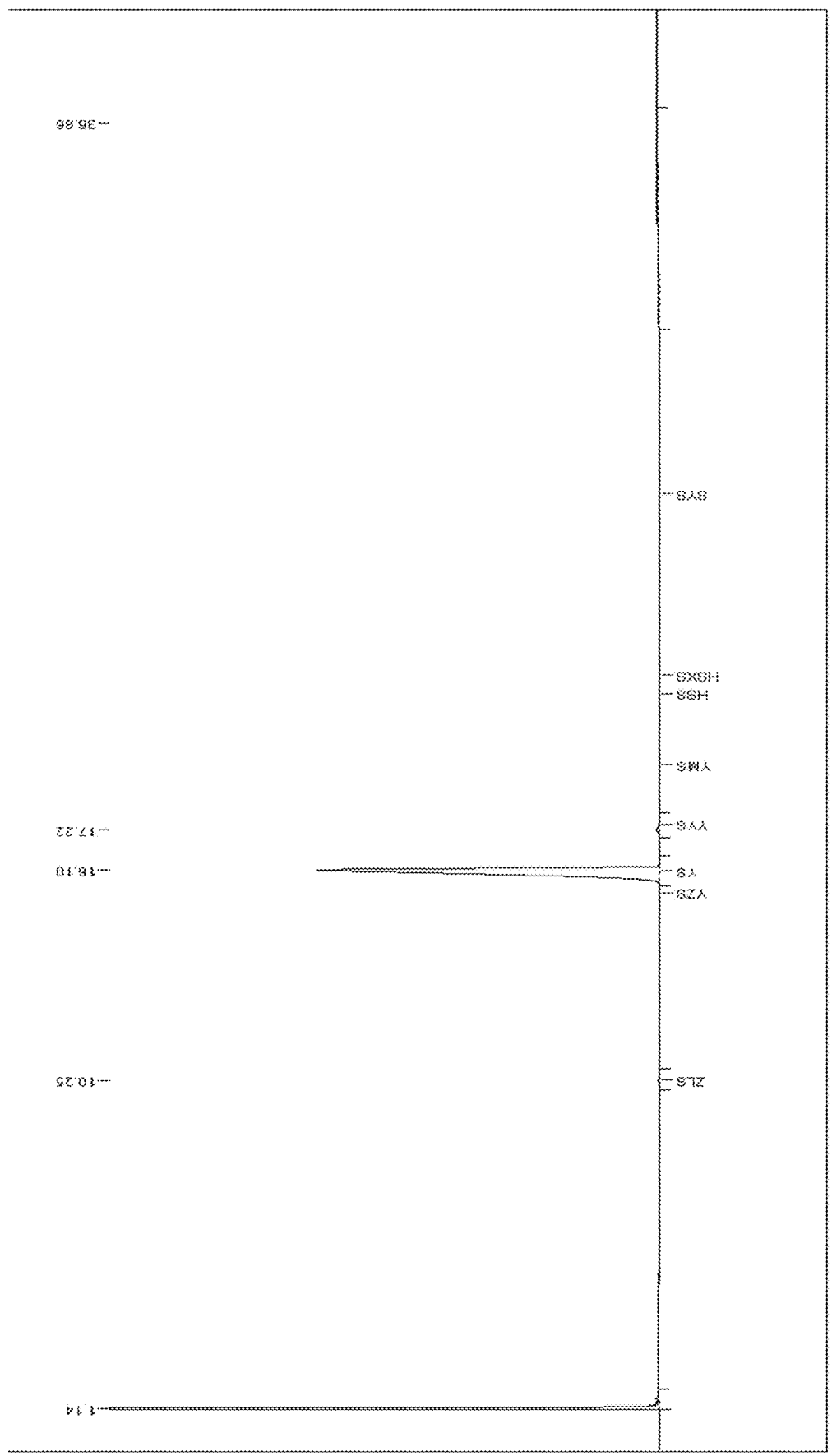
Figure 15:
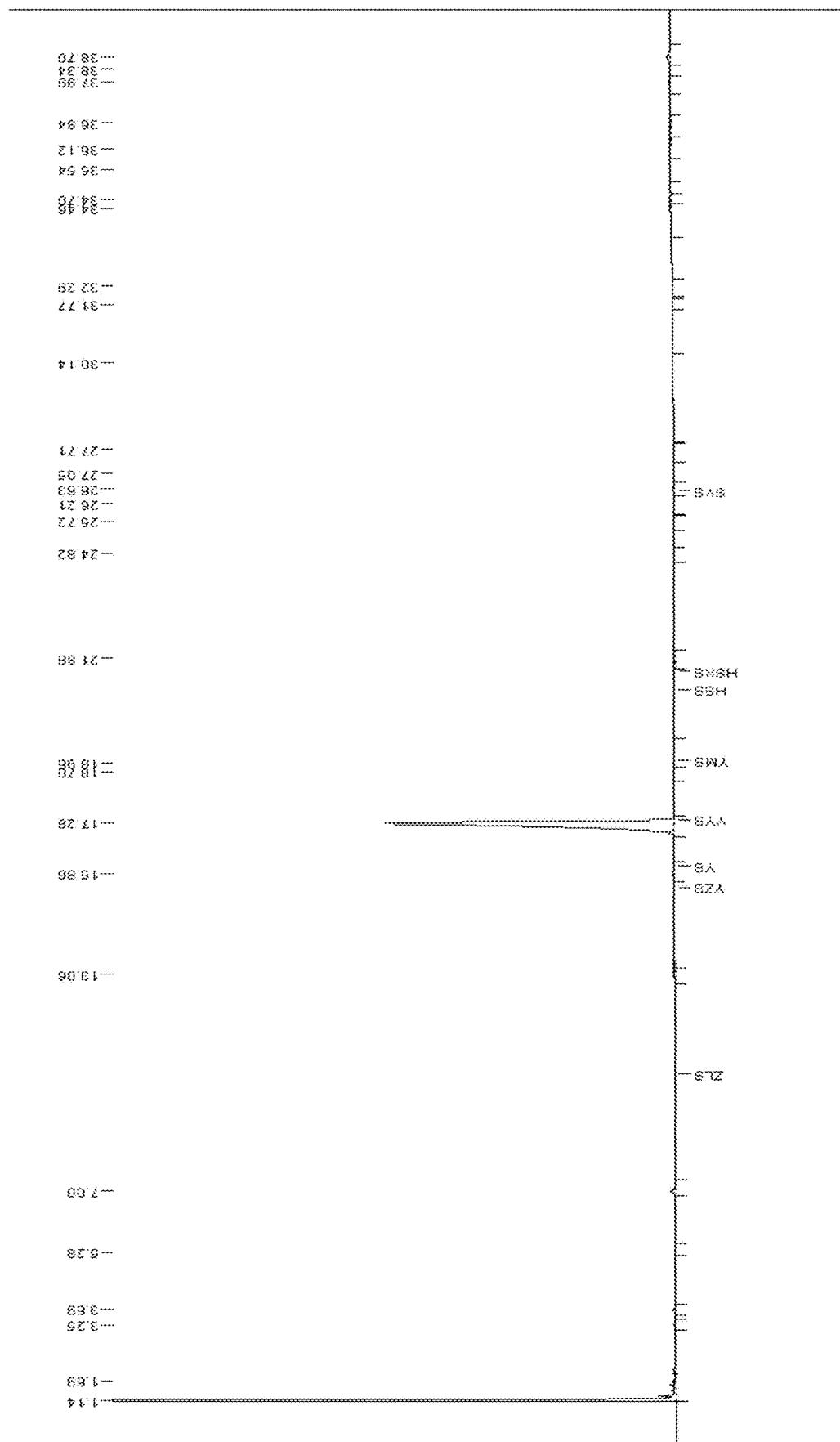

Isooctane reagent was taken and tested according to the above GC conditions. See FIG. 7 for the chromatogram.

1.6 Identification of 8 Types of Standard Chromatographic Peaks

The 8 types of FAME control products prepared above were taken and tested according to the above GC conditions. See FIGS. 8-15 for the chromatograms.

2 Study on the Experimental Method 2.1 Study on the Precision of Instrument

Semen Ziziphi Spinosae oil sample 2 was taken to prepare test solution according to the preparation method under the item "3. Preparation of test solution", and the resulting test solution was injected repeatedly for 6 times to investigate the precision of the instrument according to the experimental conditions under the item "4. Gas chromatographic conditions". The results showed that, the relative retention time RSDs of the consensus fingerprint peaks were all below 0.12% and the relative peak area RSDs were all below 5%, suggesting the instrument had a great precision. See Tables 24-25 for the results.

TABLE 24

Instrumental Precision Experiment Results (Retention Time)

| Sample | 1 | 2 | 3 | 4 | 5 | 6 | Mean | RSD(%) |
|---|---|---|---|---|---|---|---|---|
| Peak 1 | 0.638 | 0.639 | 0.638 | 0.638 | 0.638 | 0.638 | 0.6381 | 0.04 |
| Peak 2 | 0.962 | 0.963 | 0.962 | 0.963 | 0.962 | 0.962 | 0.9621 | 0.04 |
| Peak s | 1.000 | 1.000 | 1.000 | 1.000 | 1.000 | 1.000 | 1.0000 | 0.00 |
| Peak 4 | 1.079 | 1.081 | 1.080 | 1.080 | 1.080 | 1.080 | 1.0800 | 0.03 |
| Peak 5 | 1.184 | 1.184 | 1.183 | 1.184 | 1.184 | 1.184 | 1.1837 | 0.01 |
| Peak 6 | 1.228 | 1.229 | 1.227 | 1.229 | 1.228 | 1.228 | 1.2282 | 0.05 |
| Peak 7 | 1.250 | 1.250 | 1.249 | 1.250 | 1.250 | 1.250 | 1.2496 | 0.02 |
| Peak 8 | 1.306 | 1.307 | 1.306 | 1.307 | 1.307 | 1.306 | 1.3064 | 0.03 |
| Peak 9 | 1.338 | 1.340 | 1.342 | 1.338 | 1.339 | 1.338 | 1.3391 | 0.12 |
| Peak 10 | 1.372 | 1.374 | 1.372 | 1.372 | 1.373 | 1.372 | 1.3726 | 0.04 |
| Peak 11 | 1.652 | 1.652 | 1.652 | 1.653 | 1.652 | 1.652 | 1.6522 | 0.02 |
| Peak 12 | 1.684 | 1.684 | 1.684 | 1.685 | 1.684 | 1.684 | 1.6842 | 0.02 |
| Peak 13 | 1.986 | 1.986 | 1.986 | 1.986 | 1.987 | 1.986 | 1.9861 | 0.02 |

TABLE 25

Instrumental Precision Experiment Results (Peak Area)

| Sampling Sequence | 1 | 2 | 3 | 4 | 5 | 6 | Mean | RSD (%) |
|---|---|---|---|---|---|---|---|---|
| Peak 1 | 0.114 | 0.114 | 0.114 | 0.114 | 0.114 | 0.114 | 0.1140 | 0.20 |
| Peak 2 | 0.065 | 0.064 | 0.065 | 0.064 | 0.064 | 0.064 | 0.0644 | 0.30 |
| Peak s | 1.000 | 1.000 | 1.000 | 1.003 | 1.000 | 1.000 | 1.0004 | 0.11 |
| Peak 4 | 1.029 | 1.030 | 1.030 | 1.034 | 1.031 | 1.029 | 1.0305 | 0.16 |
| Peak 5 | 0.009 | 0.009 | 0.009 | 0.009 | 0.009 | 0.009 | 0.0090 | 0.54 |
| Peak 6 | 0.007 | 0.007 | 0.007 | 0.007 | 0.007 | 0.007 | 0.0069 | 0.41 |
| Peak 7 | 0.007 | 0.006 | 0.006 | 0.006 | 0.006 | 0.006 | 0.0064 | 3.89 |
| Peak 8 | 0.023 | 0.024 | 0.023 | 0.024 | 0.023 | 0.023 | 0.0233 | 2.22 |
| Peak 9 | 0.070 | 0.071 | 0.070 | 0.071 | 0.070 | 0.071 | 0.0706 | 0.41 |
| Peak 10 | 0.003 | 0.003 | 0.003 | 0.003 | 0.003 | 0.003 | 0.0027 | 2.15 |
| Peak 11 | 0.021 | 0.021 | 0.020 | 0.021 | 0.020 | 0.020 | 0.0205 | 0.55 |
| Peak 12 | 0.008 | 0.008 | 0.008 | 0.008 | 0.008 | 0.008 | 0.0078 | 3.72 |
| Peak 13 | 0.010 | 0.010 | 0.011 | 0.011 | 0.010 | 0.010 | 0.0104 | 2.79 |

2.2 Reproducibility of Method 6 portions of Semen Ziziphi Spinosae oil sample 2 were taken and prepared into test solutions according to the preparation method under the item "3. Preparation of test article solution", and the resulting test solutions were injected and tested according to the experimental conditions under the item "4. Gas chromatographic conditions". The results showed that, the relative retention time RSDs of the consensus fingerprint peaks were all below 0.09% and the relative peak area RSDs were all below 5%. See Tables 26-27 for the results.

TABLE 26

Reproducibility of Method Experiment Results (Retention Time)

| Sample | 1 | 2 | 3 | 4 | 5 | 6 | Mean | RSD(%) |
|---|---|---|---|---|---|---|---|---|
| Peak 1 | 0.638 | 0.639 | 0.638 | 0.639 | 0.639 | 0.639 | 0.6386 | 0.07 |
| Peak 2 | 0.963 | 0.963 | 0.962 | 0.963 | 0.963 | 0.963 | 0.9628 | 0.03 |
| Peak s | 1.000 | 1.000 | 1.000 | 1.000 | 1.000 | 1.000 | 1.0000 | 0.00 |
| Peak 4 | 1.079 | 1.080 | 1.080 | 1.079 | 1.079 | 1.080 | 1.0796 | 0.05 |
| Peak 5 | 1.185 | 1.186 | 1.184 | 1.185 | 1.185 | 1.186 | 1.1851 | 0.05 |
| Peak 6 | 1.230 | 1.231 | 1.230 | 1.231 | 1.231 | 1.232 | 1.2305 | 0.06 |
| Peak 7 | 1.251 | 1.252 | 1.251 | 1.252 | 1.251 | 1.252 | 1.2514 | 0.05 |
| Peak 8 | 1.308 | 1.308 | 1.307 | 1.308 | 1.308 | 1.310 | 1.3082 | 0.06 |
| Peak 9 | 1.339 | 1.341 | 1.339 | 1.340 | 1.340 | 1.342 | 1.3401 | 0.07 |
| Peak 10 | 1.374 | 1.374 | 1.374 | 1.374 | 1.375 | 1.376 | 1.3746 | 0.06 |
| Peak 11 | 1.654 | 1.655 | 1.654 | 1.655 | 1.656 | 1.657 | 1.6551 | 0.07 |
| Peak 12 | 1.686 | 1.688 | 1.686 | 1.687 | 1.688 | 1.690 | 1.6874 | 0.09 |
| Peak 13 | 1.989 | 1.990 | 1.988 | 1.990 | 1.989 | 1.992 | 1.9896 | 0.07 |

TABLE 27

Reproducibility of Method Experiment Results (Peak Area)

| Sampling Sequence | 1 | 2 | 3 | 4 | 5 | 6 | Mean | RSD (%) |
|---|---|---|---|---|---|---|---|---|
| Peak 1 | 0.112 | 0.112 | 0.110 | 0.112 | 0.111 | 0.111 | 0.1113 | 0.20 |
| Peak 2 | 0.063 | 0.063 | 0.062 | 0.064 | 0.063 | 0.063 | 0.0629 | 0.30 |
| Peak s | 1.000 | 1.000 | 1.000 | 1.000 | 1.000 | 1.000 | 1.0000 | 0.11 |
| Peak 4 | 0.894 | 0.962 | 0.991 | 0.895 | 0.962 | 0.966 | 0.9450 | 0.16 |
| Peak 5 | 0.008 | 0.007 | 0.007 | 0.008 | 0.009 | 0.009 | 0.0081 | 0.54 |
| Peak 6 | 0.046 | 0.035 | 0.030 | 0.046 | 0.035 | 0.032 | 0.0372 | 0.41 |
| Peak 7 | 0.042 | 0.033 | 0.028 | 0.042 | 0.033 | 0.028 | 0.0344 | 3.22 |
| Peak 8 | 0.024 | 0.023 | 0.023 | 0.024 | 0.024 | 0.024 | 0.0238 | 2.22 |
| Peak 9 | 0.101 | 0.093 | 0.082 | 0.102 | 0.094 | 0.093 | 0.0944 | 0.41 |
| Peak 10 | 0.007 | 0.003 | 0.003 | 0.007 | 0.003 | 0.003 | 0.0044 | 2.15 |
| Peak 11 | 0.023 | 0.021 | 0.022 | 0.023 | 0.023 | 0.022 | 0.0221 | 0.55 |
| Peak 12 | 0.006 | 0.006 | 0.006 | 0.006 | 0.006 | 0.006 | 0.0059 | 3.72 |
| Peak 13 | 0.014 | 0.011 | 0.014 | 0.012 | 0.012 | 0.015 | 0.0129 | 2.79 |

2.3 Study on the Sample Stability

Semen Ziziphi Spinosae oil sample 2 was taken and prepared into test solution according to the preparation method under the item "3. Preparation of test article solution", and the resulting test solution was tested at different time points (0 h, 3 h, 6 h, 9 h and 12 h) according to the experimental conditions under the item "4. Gas chromatographic conditions". As found by visual inspection, there was no noticeable change in the full view of the fingerprint, the overlapping was good, the relative retention time RSDs of the consensus fingerprint peaks were all below 0.08%, and the relative peak area RSDs were all below 5%, suggesting the sample had a good stability within 12 hours. See Tables 28-29 for the results.

TABLE 28

Sample Stability Experiment Results (Retention Time)

| Standing Time | 0 | 3 | 6 | 9 | 12 | Mean | RSD (%) |
|---|---|---|---|---|---|---|---|
| Peak 1 | 0.638 | 0.638 | 0.638 | 0.638 | 0.638 | 0.6380 | 0.05 |
| Peak 2 | 0.961 | 0.962 | 0.962 | 0.961 | 0.962 | 0.9618 | 0.04 |
| Peak s | 1.000 | 1.000 | 1.000 | 1.000 | 1.000 | 1.0000 | 0.00 |
| Peak 4 | 1.080 | 1.080 | 1.080 | 1.080 | 1.080 | 1.0802 | 0.02 |
| Peak 5 | 1.184 | 1.184 | 1.184 | 1.183 | 1.183 | 1.1834 | 0.04 |
| Peak 6 | 1.229 | 1.228 | 1.228 | 1.227 | 1.228 | 1.2280 | 0.04 |
| Peak 7 | 1.250 | 1.250 | 1.250 | 1.249 | 1.249 | 1.2497 | 0.04 |
| Peak 8 | 1.307 | 1.307 | 1.306 | 1.306 | 1.306 | 1.3064 | 0.03 |
| Peak 9 | 1.339 | 1.339 | 1.339 | 1.337 | 1.338 | 1.3383 | 0.06 |
| Peak 10 | 1.373 | 1.373 | 1.372 | 1.372 | 1.372 | 1.3724 | 0.05 |
| Peak 11 | 1.655 | 1.654 | 1.653 | 1.651 | 1.653 | 1.6532 | 0.08 |
| Peak 12 | 1.685 | 1.686 | 1.684 | 1.683 | 1.685 | 1.6847 | 0.07 |
| Peak 13 | 1.989 | 1.989 | 1.987 | 1.985 | 1.988 | 1.9875 | 0.08 |

TABLE 29

Sample Stability Experiment Results (Peak Area)

| Standing Time | 0 | 3 | 6 | 9 | 12 | Mean | RSD (%) |
|---|---|---|---|---|---|---|---|
| Peak 1 | 0.114 | 0.114 | 0.114 | 0.114 | 0.114 | 0.114 | 0.26 |
| Peak 2 | 0.065 | 0.064 | 0.064 | 0.065 | 0.065 | 0.065 | 0.63 |
| Peak s | 1.000 | 1.000 | 1.000 | 1.000 | 1.000 | 1.000 | 0.00 |
| Peak 4 | 1.030 | 1.030 | 1.030 | 1.030 | 1.030 | 1.030 | 0.03 |
| Peak 5 | 0.009 | 0.009 | 0.009 | 0.009 | 0.009 | 0.009 | 1.57 |
| Peak 6 | 0.007 | 0.007 | 0.007 | 0.007 | 0.007 | 0.007 | 1.86 |
| Peak 7 | 0.006 | 0.006 | 0.006 | 0.006 | 0.006 | 0.006 | 0.82 |
| Peak 8 | 0.023 | 0.023 | 0.023 | 0.023 | 0.023 | 0.023 | 1.16 |
| Peak 9 | 0.070 | 0.071 | 0.071 | 0.070 | 0.071 | 0.070 | 0.38 |
| Peak 10 | 0.003 | 0.003 | 0.003 | 0.003 | 0.003 | 0.003 | 4.66 |
| Peak 11 | 0.020 | 0.021 | 0.021 | 0.021 | 0.021 | 0.020 | 1.65 |
| Peak 12 | 0.008 | 0.008 | 0.008 | 0.008 | 0.008 | 0.008 | 1.71 |
| Peak 13 | 0.011 | 0.010 | 0.011 | 0.010 | 0.010 | 0.011 | 3.02 |

3 Gas Chromatograms of Fatty Acid Components of Semen Ziziphi Spinosae Oil

Figure 16:
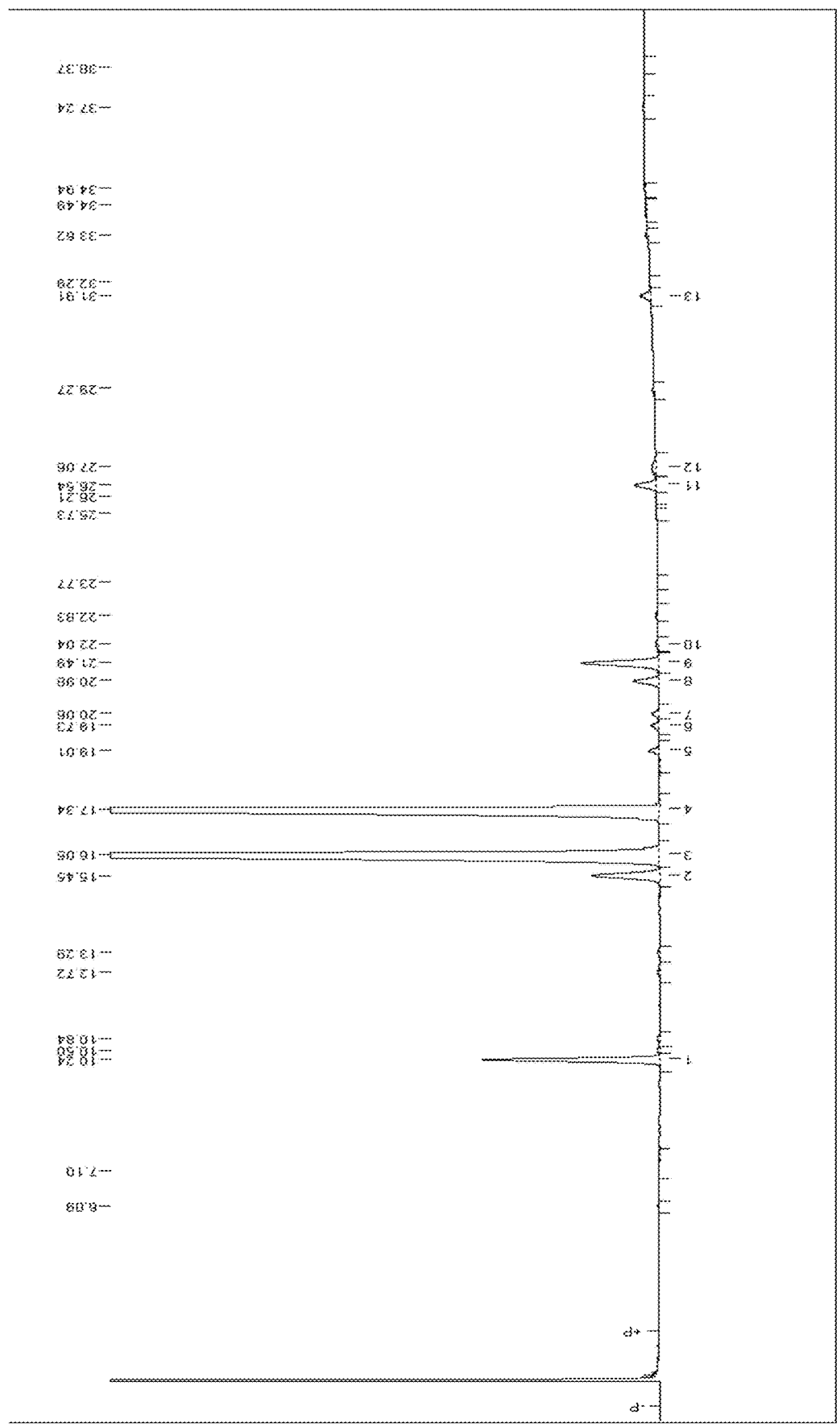
Figure 17:
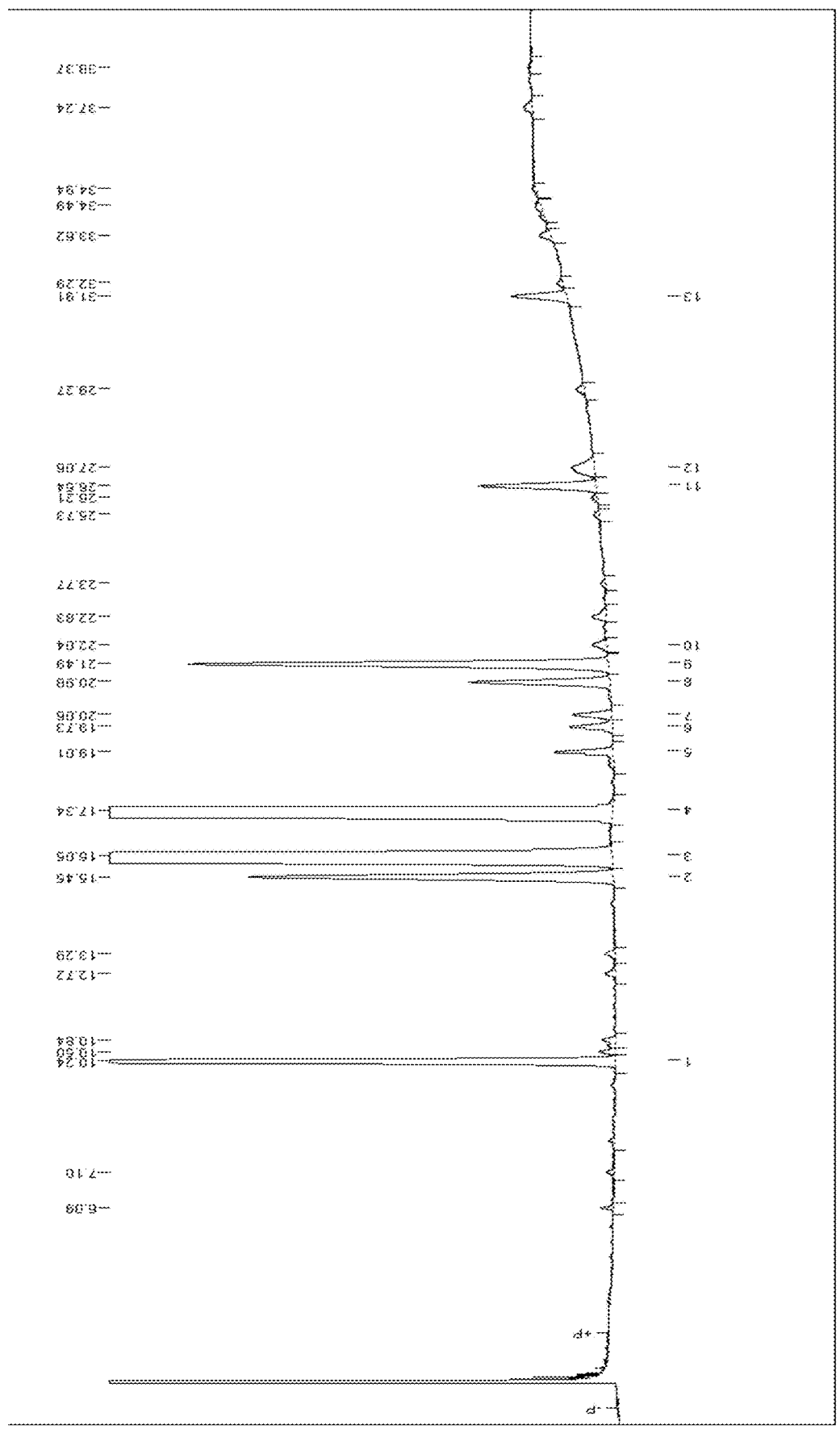

See FIGS. 16-17 for the testing results.

Analysis of results: It can be seen from the above that, there are about 31 types of fatty acid components in the Semen Ziziphi Spinosae oil, among which 13 have relatively high contents. The main components of Semen Ziziphi Spinosae oil are oleic acid, linoleic acid, palmitic acid, stearic acid, arachidic acid, arachidonic acid and behenic acid, among which the oleic/linoleic acid content ratio is about 1:1, and the sum of the two accounts for about 85% of all the components.

The invention claimed is:

1. A method for treating medicinal insomnia, said method comprising administering to a subject in need thereof an effective amount of Semen Ziziphi Spinosae oil prepared by a process comprising pressing Semen Ziziphi Spinosae at a temperature of 80-100° C.

2. The method according to claim 1, wherein said medicinal insomnia is caused by one or more drugs selected from the group consisting of an anti-asthmatic agent, an antihypertensive agent, an anticholinergic agent, a sedative, a glucocorticoid, an analgesic, an antituberculotic agent and an antiarrhythmic agent.

3. The method according to claim 2, wherein said medicinal insomnia is caused by one or more drugs selected from the group consisting of aminophylline, ephedrine, methyldopa, clonidine, atropine, *belladonna*, chloropromazine, diazepam, prednisone, dexamethasone, prednisolone, morphine, dolantin, isoniazid, diisopyramide and procaine.

4. The method according to claim 1, wherein said Semen Ziziphi Spinosae is stir-baked before pressing.

5. The method according to claim 1, wherein said Semen Ziziphi Spinosae oil prepared by a process comprising pressing Semen Ziziphi Spinosae at a temperature of 80-100° C. given degumming, deacidification, washing, dewatering and/or decolorization treatments.

6. The method according to claim 5, wherein said degumming treatment comprises the following steps:
   (a) adding saline water into the Semen Ziziphi Spinosae oil according to the oil/water/salt ratio of (40-6):(2-5):(0.2-0.5) to produce a mixture, and
   (b) stirring the mixture.

7. The method according to claim 6, wherein said oil/water/salt weight ratio is 50:4:0.4.

8. The method according to claim 6, wherein the oil temperature in said degumming does not exceed 80° C.

9. The method according to claim 5, wherein said deacidification treatment comprises the following steps:
   (a) adding alkaline water into the degummed Semen Ziziphi Spinosae oil according to the oil/water/alkali ratio of (40-60):(1-3):(0.1-0.3) to produce a mixture,
   (b) stirring the mixture,
   (c) precipitating the mixture overnight, and
   (d) separating the oil from the precipitate.

10. The method according to claim 9, wherein said oil/water/alkali weight ratio is 50:2:0.2.

11. The method according to claim 9, wherein the oil temperature in said deacidification does not exceed 75° C.

12. The method according to claim 5, wherein said washing treatment comprises the following steps:
   (a) adding water into the deacidified Semen Ziziphi Spinosae oil according to the oil/water ratio of (40-60):(4-6) to produce a mixture,
   (b) stirring the mixture,
   (c) allowing the mixture to stand still and removing any precipitate, and
   (d) removing the oil.

13. The method according to claim 12, wherein said oil/water weight ratio is 50:5.

14. The method according to claim 12, wherein the oil temperature in said washing does not exceed 80° C.

\* \* \* \* \*